US007252818B2

(12) United States Patent
Stegmann

(10) Patent No.: US 7,252,818 B2
(45) Date of Patent: Aug. 7, 2007

(54) METHOD OF PRODUCING BIOLOGICALLY ACTIVE HUMAN ACIDIC FIBROBLAST GROWTH FACTOR AND ITS USE IN PROMOTING ANGIOGENESIS

(75) Inventor: Thomas J. Stegmann, Petersberg (DE)

(73) Assignee: CardioVascular BioTherapeutics, Inc., Las Vegas, NV (US)

( * ) Notice: Subject to any disclaimer, the term of this patent is extended or adjusted under 35 U.S.C. 154(b) by 34 days.

(21) Appl. No.: 10/649,480

(22) Filed: Aug. 27, 2003

(65) Prior Publication Data

US 2004/0115769 A1 Jun. 17, 2004

Related U.S. Application Data

(63) Continuation-in-part of application No. 09/929,945, filed on Aug. 15, 2001, now Pat. No. 6,642,026, and application No. 10/649,480, which is a continuation-in-part of application No. 09/358,780, filed on Jul. 22, 1999, now abandoned.

(60) Provisional application No. 60/225,406, filed on Aug. 15, 2000, provisional application No. 60/093,962, filed on Jul. 24, 1998.

(51) Int. Cl.
*A16K 38/00* (2006.01)
*C07K 14/50* (2006.01)
(52) U.S. Cl. .................. 424/93.1; 530/350; 530/300
(58) Field of Classification Search .............. 424/93.1, 424/93.2; 435/69.1; 530/350, 380, 300
See application file for complete search history.

(56) References Cited

U.S. PATENT DOCUMENTS

| | | | |
|---|---|---|---|
| 4,444,760 A | 4/1984 | Thomas, Jr. | |
| 4,642,120 A | 2/1987 | Nevo et al. | |
| 4,693,995 A | 9/1987 | Prino et al. | |
| 5,209,776 A | 5/1993 | Bass et al. | |
| 5,401,832 A * | 3/1995 | Linemeyer et al. | 530/399 |
| 5,520,191 A | 5/1996 | Karlsson et al. | |
| 5,571,790 A * | 11/1996 | Jaye et al. | 514/12 |
| 5,683,989 A | 11/1997 | Lau et al. | |
| 5,792,453 A | 8/1998 | Hammond et al. | |
| 5,814,462 A | 9/1998 | Weinberger | |
| 5,827,826 A | 10/1998 | Jaye et al. | |
| 6,045,565 A * | 4/2000 | Ellis et al. | 606/167 |
| 6,060,454 A | 5/2000 | Duhaylongsod | |
| 6,268,178 B1 | 7/2001 | Kordyum et al. | |
| 6,773,899 B2 * | 8/2004 | Kordyum et al. | 435/69.1 |

FOREIGN PATENT DOCUMENTS

| | | |
|---|---|---|
| EP | 0 298 723 A1 | 1/1989 |
| SU | 1 089 119 | 4/1984 |
| WO | WO 92/09301 | 6/1992 |
| WO | WO 92/13565 | 9/1992 |
| WO | WO 98/39436 | 9/1998 |

OTHER PUBLICATIONS

Schumacher e tal. Circulation, 1998, vol. 97, pp. 645-650.*
Fasol. et al. The Journal of Thoracic and Cardiovascular Surgery, 1994, vol. 107, pp. 1432-1439.3.*
Htun et al. J. Mol. Cell Cardiol. 1998, vol. 30, pp. 867-877.*
Pu et al. Circulation 1993, vol. 88, No. 1, pp. 208-215.*
Battegay E.J. 1995, vol. 73, pp. 333-346.*
Banai et al. Circ. Res. 1991, vol. 69, No. 1, pp. 76-85.*
Hendel, et al. "Effect of Intracoronary Recombinant Human Vascular Endothelial Growth Factor on Myocardial Perfusion," *Circulation*, vol. 101, pp. 118-121, 2000.
Laham, et al. "Subxyphoid Access of the Normal Pericardium: A Novel Drug Delivery Technique," *Catheterization and Cardiovascular Interventions*, vol. 47, pp. 109-111, 1999.
Laham, et al. "Local Perivascular Delivery of Basic Fibroblast Growth Factor in Patients Undergoing Coronary Bypass Surgery, Results of a Phase I Randomized, Double-Blind, Placebo-Controlled Trial," *Circulation*, vol. 100, pp. 1865-1871, 1999.
Rosengart, et al. "Angiogenesis Gene Therapy, Phase I Assessment of Direct Intramyocardial Administration of an Adenovirus Vector Expressing VEGF121 cDNA to Individuals with Clinically Significant Severe Coronary Artery Disease," *Circulation*, vol. 100, pp. 468-474, 1999.
Stegmann, et al. "First Angiogenic Treatment of Coronary heart Disease by FGF-1: Long-Term Results After 3 years," *Cardiac and Vascular Regeneration*, vol. 1, No. 1, pp. 5-10, Mar. 2000.
Symes, et al. "Gene Therapy with Vascular Endothelial Growth Factor for Inoperable Coronary Artery Disease," *Annals of Thoracic Surgery*, vol. 68, pp. 830-837, 1999.
Udelson, et al. "Therapeutic Angiogenesis with Recombinant Fibroblast Growth Factor-2 Improves Stress and Rest Myocardial Perfusion Abnormalities in Patients with Severe Symptomatic Chronic Coronary Artery Disease," *Circulation*, vol. 102, pp. 1605-1610, 2000.
Waxman, et al. "Persistent Primary Coronary Dilation Induced by Transatrial Delivery of Nitroglycerin into the Pericardial Space: A Novel Approach for Local Cardiac Drug Delivery," *Journal of the American College of Cardiology*, vol. 33, No. 7, pp. 2073-2077, Jun. 1999.
Sorochinskaya, et al. "Study of Beta Lactamase Tem1 Synthesis in Various *Escherichia coli* Strains Infected by the Phage Lambda-BLA with Amber Mutations in Different Regulatory Genes," *Biopolimery I Kletka*, vol. 7, No. 1, pp. 101-107, 1991 (abstract).
Watanabe, et al. "Molecular Characterization of Recombinant Human Acidic Fibroblast Growth Factor Produced in *E. coli*: Comparative Studies with Human Basic Fibroblast Growth Factor," *Molecular Endocrinology*, vol. 4, No. 6, pp. 869-879, 1990.

(Continued)

*Primary Examiner*—Bruce R. Campell
*Assistant Examiner*—Bao Qun Li
(74) *Attorney, Agent, or Firm*—Knobbe, Martens, Olson & Bear, LLP

(57) ABSTRACT

The present invention relates to the treatment of coronary heart disease by revascularization therapy, and more particularly to the intramyocardial injection of a pharmaceutical composition comprising a recombinant fibroblast growth factor-1 protein or a fragment of a recombinant fibroblast growth factor-1 protein, optionally, with a physiologic glue for inducing local neoangiogenesis in ischemic myocardium. Methods of producing the recombinant fibroblast growth factor 1 protein and fragments are also disclosed.

17 Claims, 18 Drawing Sheets

OTHER PUBLICATIONS

Zazo, et al. "High-Level Synthesis in *Escherichia coli* of Shortened and Full-Length Human Acidic Fibroblast Growth Factor and Purification in a Form Stable in Aqueous Solutions," *Gene*, vol. 113, No. 2, pp. 231-238, Jan. 1992.

Supplementary European Search Report completed May 31, 2005 and issued to a related foreign application.

Lei, et al. "Effects of Ribosomal Protein Mutations on the Expression of Bacteriophage Lambda N Gene in *Escherichia-coli*," *Acta Genetica Sinica*, vol. 14, No. 4, pp. 318-322, 1987, Abstract only.

Ratajska, et al. "Modulation of cell migration and vessel formation by vascular endothelial growth factor and basic fibroblast growth factor in cultured embryonic heart," *Developmental Dynamics*, 1995, 203/4, pp. 399-407.

Sellke, et al. "Enhanced microvascular relaxations to VEGF and bFGF in chronically ischemic porcine myocardium," *American journal of Physiology*, 1996 271/2, pp. 713-720.

Fasol, et al. "Experimental use of a modified fibrin glue to induce site-directed angiogenesis from the aorta to the heart," *Journal of Thoracic Cardiovascular Surgery*, Jun. 1994, pp. 1432-1439.

Weatherford, et al. "Vascular endothelial growth factor and heparin in a biologic glue promotes human aortic endothelial cell proliferation with aortic smooth muscle cell inhibition," *Surgery*, Aug. 1996, 120(2), pp. 433-439.

Kang, et al. Selective stimulation of endothelial cell proliferation with inhibition of smooth muscle cell proliferation by fibroblast-growth factor-1 plus heparin delivered from fibrin glue suspensions, *Surgery*, Aug. 1995, 118(2), pp. 280-286, discussion pp. 286-287.

Watabene, et al. "Effect of basic fibroblast growth factor on angiogenesis in the infarcted porcine heart," *Basic Research in Cardiology*, Feb. 1998, 93(1), pp. 30-37.

Lopez. "Angiogenic potential of perivascularly delivered aFGF in a porcine model of chronic myocardial ischemia," *American journal of Physiology*, Mar. 1998, 274, pp. 930-936.

Schumacher, et al. "Induction of neoangiogenesis in ischemic myocardium by human growth factors, first clinical results of a new treatment of coronary heart disease," *Circulation*, Feb. 24, 1998, 97(7), pp. 645-650.

Lazarous et al. "Pharmacodynamics of basic fibroblast growth factor: route of administration determines myocardial and systemic distribution," *Cardiovascular Research*, Oct. 1997, 36(1), pp. 78-85.

Scheinowitz, et al. "The role of insulin-like and basic fibroblast growth factors on ischemic and infarcted myocardium: a mini review," *International Journal of Cardiology*, Mar. 1997, 59(1), pp. 1-5.

Shou, et al. "Effect of basic fibroblast growth factor on myocardial angiogenesis in dogs with mature collateral vessels," Journal of American College of Cardiology, Apr. 1997, 29(5), pp. 1102-1106.

Gu, "Basic fibroblast growth factor as a biochemical marker of exercise-induced ischemia," *Circulation*, Mar. 4, 1997, 95(5), pp. 1165-1168.

Horrigan, et al. "Reduction in myocardial infarct size by basic fibroblast growth factor after temporary coronary occlusion in a canine model," *Circulation*, Oct. 15, 1996, 94(8), pp. 1927-1933.

Schaper, "Collateral vessel growth in the human heart. Role of fibroblast growth factor-2," *Circulation*, Aug. 15, 1996, 94(4), pp. 600-601.

Sellke, et al. "Angiogenesis induced by acidic fibroblast growth factor as an alternative method of revascularization for chronic myocardial ischemia," *Surgery*, Aug. 1996, 120(2), pp. 182-188.

Uchida, et al. "Angiogenic therapy of acute myocardial infarction by intrapericardial injection of basic fibroblast growth factor and heparin sulfate: an experimental study," *American Heart Journal*, Dec. 1995, 130(6), pp. 1182-1188.

Slavin, "Fibroblast growth factors: at the heart of angiogenesis," *Cell Biology International*, May 1995, 19(5), pp. 431-444.

Landau, et al. "Intrapericardial basic fibroblast growth factor induces myocardial angiogenesis in a rabbit model of chronic ischemia," *American Heart Journal*, May 1995, 129(5), pp. 924-931.

Schlaudraff, et al. "Growth of "new" coronary vascular structures by angiogenetic growth factors," *European Journal of Cardiothoracic Surgery*, 1993 7(12), pp. 937-943.

Battler, et al. "Intracoronary injection of basic fibroblast growth factor enhances angiogenesis in infarcted swine myocardium," *Journal of American College of Cardiology*, Dec. 1993, 22(7), pp. 2001-2006.

Unger, et al. "Extracardiac to coronary anastomoses support regional left ventricular function in dogs," *American Journal of Physiology*, May 1993, 264, pp. 1567-1574.

Engelmann, "Acidic fibroblast growth factor and heart development. Role in myocyte proliferation and capillary angiogenesis," *Circulation Research*, Jan. 1993 27(1), pp. 7-19.

Yanagisawa-Miwa, et al. "Salvage of infarcted myocardium by angiogenic action of basic fibroblast growth factor," *Science*, Sep. 4, 1992, 257, pp. 1401-1403.

Engelmann, et al. "Acidic fibroblast growth factor, heart development, and capillary angiogenesis," *Annual New York Academy of Science*, 1991, 638, pp. 463-466.

Schaper, "Angiogenesis in the adult heart," *Basic Research in Cardiology*, 1991, 86, Suppl. 2, pp. 51-56.

Banai, et al. "Effects of acidic fibroblast growth factor on normal and ischemic myocardium" *Circulation Research*, Jul. 1991, 69(1), pp. 76-85.

Consigli, et al. "Immunolocalization of basic fibroblast growth factor during chicken cardiac development," *Journal of Cell Physiology* Mar. 1991, 146(3), pp. 379-385.

Schaper, et al. "Molecular biologic concepts of coronary anastomoses," *Journal of American College of Cardiology*, Mar. 1, 1009, 15(3), pp. 513-518.

Lopez, et al. "Local extravascular growth factor delivery in myocardial ischemia," *Drug Delivery: Journal of Delivery and Targeting and Therapeutic Agents*, 1996 3(3).

Simons, et al. "Food for starving hearts," *National Medical*, vol. 2, No. 5, pp. 519-520.

Barrios, et al. "Angiogenesis in the rate heart induced by local delivery of basic fibroblast growth factor," XVIIth Congress of the European Society of Cardiology, Amsterdam (The Netherlands), Aug. 20-24, 1995.

Ueno, et al. "Adenovirus-mediated expression of the secreted form of basic fibroblast growth factor (FGF-2) induces cellular proliferation and angiogenesis in vivo," *Arteriosclerosis Thrombosis and Vascular Biology*, 17(11), 1997, pp. 2453-2460.

Symes, "Therapeutic angiogenesis for coronary artery and peripheral vascular disease," *Journal of Molecular and Cellular Cardiology*, 29(7), A268.

Zarge, et al. "Fibrin glue containing fibroblast growth factor type 1 and heparin decreases platelet deposition," *The American Journal of Surgery*, vol. 174, Aug. 1997, pp. 188-192.

Albes, et al. "Improvement of tracheal autograft revascularization by means of fibroblast growth factor," *The Annals of Thoracic Surgery*, 1994, vol. 57, pp. 444-449.

Folkman, "Angiogenic therapy of the human heart," *Circulation*, 1998, vol. 97, pp. 628-629.

Forough, et al. "Differential expression in *Escherichia coli* of the α and β form of heparin-binding acidic fibroblast growth factor-1: potential role of RNA secondary structure," *Biochemica et Biophysica Acta*, 1090, 1991, pp. 293-298.

Cheng, et al. "Characterization of fibrin glue-gdnf slow-release preparation," *Cell Transplantation*, vol. 7, No. 1, 1998, pp. 53-61I.

Cuevas, et al. "Protection of rat myocardium by mitogenic and non-mitogenic fibroblast growth factor during post-ischemic reperfusion," *Growth Factors*, vol. 15, 1997, pp. 29-40.

Giordano, et al. "Intracoronary gene transfer of fibroblast growth factor-5 increases blood flow and contractile function in an ishemic region of the heart," *Nature Medicine*, vol. 2, No. 5, May 1996, pp. 534-539.

Oyama, et al. "The effect of basic fibroblast growth factor (bFGF) on early bronchial revascularization," *Nippon Kyobu Geka Gakkai Zasshi*, Nov. 1996, vol. 44, No. 11, pp. 2032-2039 (Abstract only).

Xie, et al. "The capillary of left ventricular tissue of rats subjected to coronary artery occlusion," *Cardiovascular Research*, Mar. 1997, vol. 33, No. 3, pp. 671-676.

Gimenez-Gallego, et al. "Brain-derived acidic fibroblast growth factor: complete amino acid sequence and homologies," *Science*, vol. 230, Dec. 1985, pp. 1385-1388.

Gospodarowicz, et al. "Isolation of brain fibroblast growth factor by heparin-sepharose affinity chromatography: identity with pituitary fibroblast growth factor," *Procedures of the National Academy of Sciences*, vol. 81, No. 1984, pp. 6963-6967.

Jaye, et al. "Human endothelial cell growth factor: cloning, nucleotide sequence, and chromosome localization," *Science*, vol. 233, Aug. 1986, pp. 541-545.

Harper, et al. "Human class 1 heparin-binding growth factor: structure and homology to bovine acidic brain fibroblast growth factor," *Biochemistry*, 1986, vol. 25, pp. 4097-4103.

Amoroso, et al. "Vascular endothelial growth factor: a key mediator of neoangiogenesis. A review," *European Review for Medical and Pharmacological Sciences*, Jan. 1997, vol. 1, No. 1-3, pp. 17-25.

Schlaudraff, et al. "Induction of new functional blood vessels in humans by the first administration of human growth factor HBGF-1," English summary only.

Zarge, et al. "Platelet deposition on ePTFE grafts coated with fibrin glue with or without FGF-1 and heparin," *Journal of Surgical Research*, vol. 67, No. 1, pp. 4-8.

Gonçalves. "Angiogenic growth factors: potential new treatment for acute myocardial infarction?" *Cardiovascular Research*, 45, 2000, pp. 294-302.

Blaber, et al. *Biophysical Journal*, vol. 77, 1999, pp. 470-477.

Strickberger, *Genetics*, The Macmillan Company, New York, 1968, p. 202.

Winkles, et al. "Human vascular smooth muscle cells both express and respond to heparin-binding growth factor I (endothelial cell growth factor)," *Procedures of the National Academy of Sciences*, Oct. 1987, vol. 84, pp. 7124-7128.

Burgess, et al. "Structure-function studies of heparin-binding (acidic fibroblast) growth factor-1 using site-directed mutagenesis," *Journal of Cellular Biochemistry*, 1991, 45, pp. 131-138.

* cited by examiner

```
                              BsaBI
                            ---------
                  BsaBI
                -----------
         BglII          VspI          BfmI         MbiI          XbaI
        ------         ------        ------       ------        ------
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT
```

+2                                        MetAlaGluGlyGlu IleThrThrPheThrAlaLeuThrGluLysPheAsnLeuProPr
                                                          HpaI
                                                         ------
                                                                   HindII                   SmaI
                                                                  -------                   ----
                          NdeI    Eco57I                            HincII                   AvaI
                         ------   ------                           -------                   ----
```
5041 TTTTGTTTAACTTTAAGAAGGAGATATACATATGGCTGAAGGGGA AATCACCACCTTTACAGCGTTAACGGAGAAATTTAACCTTCCGCC
     AAAACAAATTGAAATTCTTCCTCTATATGTATACCGACTTCCCCT TTAGTGGTGGAAATGTCGCAATTGCCTCTTTAAATTGGAAGGCGG
```

+2 oGlyAsnTyrLysLysProLysLeuLeuTyrCysSerAsnGlyGly HisPheLeuArgIleLeuProAspGlyThrValAspGlyThrAr
    SmaI                              PstI
    ----                             ------
   AvaI          HindIII           BfmI             EcoRI                            NruI
   ----          -------          ------           -------                           ----
```
5131 CGGGAATTACAAAAAACCCAAGCTTCTTTACTGCAGTAACGGAGG ACACTTCCTGCGAATTCTGCCAGATGGCACAGTAGATGGGACTCG
     GCCCTTAATGTTTTTTGGGTTCGAAGAAATGACGTCATTGCCTCC TGTGAAGGACGCTTAAGACGGTCTACCGTGTCATCTACCCTGAGC
```

+2 gAspArgSerAspGlnHisIleGlnLeuGlnLeuSerAlaGluSer ValGlyGluValTyrIleLysSerThrGluThrGlyGlnTyrLe
                                                    SalI
                                                   ------
    PvuI                                                             HindII                   RsaI
   ------                                                           -------                   ----
    NruI          PvuII           XmaIII                             HincII        MlsI Csp6I
    ----         ------          --------                           -------       ------------
```
5221 CGATCGCTCCGACCAGCACATTCAGCTGCAACTCTCGGCCGAAAG CGTTGGAGAGGTCTATATCAAGTCGACGGAGACTGGCCAGTACCT
     GCTAGCGAGGCTGGTCGTGTAAGTCGACGTTGAGAGCCGGCTTTC GCAACCTCTCCAGATATAGTTCAGCTGCCTCTGACCGGTCATGGA
```

+2 uAlaMetAspThrAspGlyLeuLeuTyrGlySerGlnThrProAsn GluGluCysLeuPheLeuGluArgLeuGluGluAsnHisTyrAs
    StyI
    ----
    NcoI                                                 Mval269I      XbaI
   ------                                               ---------     ------
```
5311 TGCCATGGACACCGATGGGCTTCTGTATGGCTCACAGACGCCTAA CGAAGAATGCTTGTTTCTAGAAAGACTAGAAGAAAACCATTACAA
     ACGGTACCTGTGGCTACCCGAAGACATACCGAGTGTCTGCGGATT GCTTCTTACGAACAAAGATCTTTCTGATCTTCTTTTGGTAATGTT
```

+2 nThrTyrIleSerLysLysHisAlaGluLysAsnTrpPheValGly LeuLysLysAsnGlySerCysLysArgGlyProArgThrHisTy
    RsaI
    ----
   Csp6I                          StuI
   -----                         ------
```
5401 CACGTACATATCGAAAAAACATGCAGAGAAGAACTGGTTTGTAGG CCTTAAAAAAAATGGTTCCTGTAAGCGTGGACCACGGACTCACTA
     GTGCATGTATAGCTTTTTTGTACGTCTCTTCTTGACCAAACATCC GGAATTTTTTTTACCAAGGACATTCGCACCTGGTGCCTGAGTGAT
```

+2 rGlyGlnLysAlaIleLeuPheLeuProLeuProValSerSerAsp ***
                                                                    SalI            XmaIII
                                                                   ------          --------
                              SacI                  EcoRI SacI   HindII             XhoI
                             ------                -------------- ------            ----
     MlsI                    Ecl136II     BamHI         Ecl136IIHincIIHindIII  NotIAvaI
    ------                  ---------    -------       ------------------------------
```
5491 TGGCCAAAAGGCTATCTTGTTCCTGCCACTACCAGTGAGCTCCGA CTAAGGATCCGAATTCGAGCTCCGTCGACAAGCTTGCGGCCGCAC
     ACCGGTTTTCCGATAGAACAAGGACGGTGATGGTCACTCGAGGCT GATTCCTAGGCTTAAGCTCGAGGCAGCTGTTCGAACGCCGGCGTG
```

**CHEMICALLY SYNTHESIZED haFGF GENE AND
CORRESPONDING AMINO ACID SEQUENCE**

*FIG. 1*

| | | | | | | | | |
|---|---|---|---|---|---|---|---|---|
| FGF fr HUMECGFB | TTC | GCC | CTG | ACC | AAG | AAT | CTG | CCT | CCA |
| haFGF 155 | TTT | GCG | TTA | ACG | AAA | AAC | CTT | CCG | CCC |
| № amino acid | 009 | 011 | 012 | 013 | 015 | 017 | 018 | 019 | 020 |
| | Phe | Ala | Leu | Thr | Lys | Asn | Leu | Pro | Pro |

| | | | | | | | | |
|---|---|---|---|---|---|---|---|---|
| FGF fr HUMECGFB | AAG | AAG | AAA | CTC | CTC | TGT | AGC | GGG | GGC |
| haFGF 155 | AAA | AAA | AAG | CTT | CTT | TGC | AGT | GGA | GGA |
| № amino acid | 024 | 025 | 027 | 028 | 029 | 031 | 032 | 034 | 035 |
| | Lys | Lys | Lys | Leu | Leu | Cys | Ser | Gly | Gly |

| | | | | | | | | |
|---|---|---|---|---|---|---|---|---|
| FGF fr HUMECGFB | AGG | ATC | CTT | CCG | GTG | ACA | AGG | GAC | AGG |
| haFGF 155 | CGA | ATT | CTG | CCA | GTA | ACT | CGC | GAT | CGC |
| № amino acid | 039 | 040 | 041 | 042 | 046 | 049 | 050 | 051 | 052 |
| | Arg | Ile | Leu | Pro | Val | Thr | Arg | Asp | Arg |

| | | | | | | | | |
|---|---|---|---|---|---|---|---|---|
| FGF fr HUMECGFB | AGC | CAG | AGT | GCG | GTG | GGG | GTG | ATA | AGT |
| haFGF 155 | TCC | CAA | TCG | GCC | GTT | GGA | GTC | ATC | TCG |
| № amino acid | 053 | 060 | 062 | 063 | 066 | 067 | 069 | 071 | 073 |
| | Ser | Gln | Ser | Ala | Val | Gly | Val | Ile | Ser |

| | | | | | | | | |
|---|---|---|---|---|---|---|---|---|
| FGF fr HUMECGFB | ACC | TTG | GAC | TTA | TAC | ACA | CCA | AAT | GAG |
| haFGF 155 | ACG | CTT | GAT | CTG | TAT | ACG | CCT | AAC | GAA |
| № amino acid | 074 | 080 | 085 | 088 | 089 | 093 | 094 | 095 | 096 |
| | Thr | Leu | Asp | Leu | Tyr | Thr | Pro | Asn | Glu |

| | | | | | | | | |
|---|---|---|---|---|---|---|---|---|
| FGF fr HUMECGFB | TGT | TTC | CTG | AGG | CTG | GAG | GAG | ACC | TAT |
| haFGF 155 | TGC | TTT | CTA | AGA | CTA | GAA | GAA | ACG | TAC |
| № amino acid | 098 | 100 | 101 | 103 | 104 | 105 | 106 | 111 | 112 |
| | Cys | Phe | Leu | Arg | Leu | Glu | Glu | Thr | Tyr |

| | | | | | | | | |
|---|---|---|---|---|---|---|---|---|
| FGF fr HUMECGFB | TCC | AAG | AAG | AAT | GTT | CTC | AAG | AAG | GGG |
| haFGF 155 | TCG | AAA | AAA | AAC | GTA | CTT | AAA | AAA | GGT |
| № amino acid | 114 | 115 | 116 | 121 | 124 | 126 | 127 | 128 | 130 |
| | Ser | Lys | Lys | Asn | Val | Leu | Lys | Lys | Gly |

| | | | | | | | | |
|---|---|---|---|---|---|---|---|---|
| FGF fr HUMECGFB | AGC | TGC | AAA | CGC | GGT | CCT | CAG | AAA | GCA |
| haFGF 155 | TCC | TGT | AAG | CGT | GGA | CCA | CAA | AAG | GCT |
| № amino acid | 131 | 132 | 133 | 134 | 135 | 136 | 142 | 143 | 144 |
| | Ser | Cys | Lys | Arg | Gly | Pro | Gln | Lys | Ala |

| | | | | | | | | |
|---|---|---|---|---|---|---|---|---|
| FGF fr HUMECGFB | TTT | CTC | CCC | CTG | GTC | TCT | TCT | GAT | |
| haFGF 155 | TTC | CTG | CCA | CTC | GTG | AGC | TCC | GAC | |
| № amino acid | 147 | 148 | 149 | 150 | 152 | 153 | 154 | 155 | |
| | Phe | Leu | Pro | Leu | Val | Ser | Ser | Asp | |

MODIFICATION IN MOLECULE haFGF 155 CODONS.
FGF fr HUMECGFB–THE SEQUENCE FROM GENBANK(at NCBI), haFGF 155
–THE SEQUENCE SYNTHESIZED BY THE INVENTION AUTHORS.

*FIG. 2*

FGF-1(154aa) PURIFICATION

LANE 1: CRUDE MEDIA: YIELD: 225 mg FGF-1/LITER
     2: HEPARIN-SEPHAROSE COLUMN
     3: HPLC: C-18 COLUMN

OVERALL PURIFICATION YIELD: 65%
BIOACTIVITY: EQUIPOTENT WITH FGF-1 (SIGMA CHEM) IN:
       1) 3T3 CELL PROLIFERATION ASSAY, AND
       2) RAT HIND LIMB ANGIOGENESIS ASSAY

```
                BsaBI
                ------
        BsaBI
        ------
        BglII           VspI            BfmI            MbiI            XbaI
        -----           ----            ----            ----            ----
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT

+2                              MetAsnTyrLysLys ProLysLeuLeuTyrCysSerAsnGlyGlyHisPheLeuArgIl
                                                                        PstI
                                                                        ----
                NdeI                            HindIII BfmI                            EcoRI
                ----                            ------- ----                            -----
5041 TTTTGTTTAACTTTAAGAAGGAGATATACATATGAATTACAAAAA ACCCAAGCTTCTTTACTGCAGTAACGGAGGACACTTCCTGCGAAT
     AAAACAAATTGAAATTCTTCCTCTATATGTATACTTAATGTTTTT TGGGTTCGAAGAAATGACGTCATTGCCTCCTGTGAAGGACGCTTA +2 eLeuProAspGlyThrValAspGlyThrArgAspArgSerAspGln HisIleGlnLeuGlnLeuSerAlaGluSerValGlyGluValTy
                                 PvuI
                                 ----
        EcoRI           NruI            PvuII           XmaIII
        -----           ----            -----           ------
5131 TCTGCCAGATGGCACAGTAGATGGGACTCGCGATCGCTCCGACCA GCACATTCAGCTGCAACTCTCGGCCCGAAAGCGTTGGAGAGGTCTA
     AGACGGTCTACCGTGTCATCTACCCTGAGCGCTAGCGAGGCTGGT CGTGTAAGTCGACGTTGAGAGCCGGCTTTCGCAACCTCTCCAGAT +2 rIleLysSerThrGluThrGlyGlnTyrLeuAlaMetAspThrAsp GlyLeuLeuTyrGlySerGlnThrProAsnGluGluCysLeuPh
        SalI
        ----
        HindII          RsaI    StyI
        ------          ----    ----
        HincII  MlsI Csp6I NcoI                                                  Mva1269I
        ------  ---- ----- ----                                                  --------
5221 TATCAAGTCGACGGAGACTGGCCAGTACCTTGCCATGGACACCGA TGGGCTTCTGTATGGCTCACAGACGCCTAACGAAGAATGCTTGTT
     ATAGTTCAGCTGCCTCTGACCGGTCATGGAACGGTACCTGTGGCT ACCCGAAGACATACCGAGTGTCTGCGGATTGCTTCTTACGAACAA +2 eLeuGluArgLeuGluGluAsnHisTyrAsnThrTyrIleSerLys LysHisAlaGluLysAsnTrpPheValGlyLeuLysLysAsnGl
                                 RsaI
                                 ----
        XbaI                    Csp6I                                   StuI
        ----                    -----                                   ----
5311 TCTAGAAAGACTAGAAGAAAACCATTACAACACGTACATATCGAA AAAACATGCAGAGAAGAACTGGTTTGTAGGCCTTAAAAAAAATGG
     AGATCTTTCTGATCTTCTTTTGGTAATGTTGTGCATGTATAGCTT TTTTGTACGTCTCTTCTTGACCAAACATCCGGAATTTTTTTTACC +2 ySerCysLysArgGlyProArgThrHisTyrGlyGlnLysAlaIle LeuPheLeuProLeuProValSerSerAsp***
                                                                SacI
                                                                ----
                        MlsI                            Ec1136II         BamHIEcoRI
                        ----                            --------         ----------
5401 TTCCTGTAAGCGTGGACCACGGACTCACTATGGCCAAAAGGCTAT CTTGTTCCTGCCACTACCAGTGAGCTCCGACTAAGGATCCGAATT
     AAGGACATTCGCACCTGGTGCCTGAGTGATACCGGTTTTCCGATA GAACAAGGACGGTGATGGTCACTCGAGGCTGATTCCTAGGCTTAA SacI    SalI
        ----    ----
        EcoRI   HindII  XmaIII          XhoI
        -----   ------  ------          ----
        Ec1136IIHincIIHindIII NotI      AvaI
        -------------------- ----      ----
5491 CGAGCTCCGTCGACAAGCTTGCGGCCGCACTCGAGCACCACCACC ACCACCACTGAGATCCGGCTGCTAACAAAGCCCGAAAGGAAGCTG
     GCTCGAGGCAGCTGTTCGAACGCCGGCGTGAGCTCGTGGTGGTGG TGGTGGTGACTCTAGGCCGACGATTGTTTCGGGCTTTCCTTCGAC
```

NUCLEOTIDE AND AMINO ACID SEQUENCE FOR CHEMICALLY SYNTHESIZED HUMAN A FGF (134 AMINO ACIDS)

FIG. 6

```
                    BsaBI
                   ----------
         BsaBI
       ----------
          BglII           VspI            BfmI           MbiI            XbaI
        ------          ------          ------         ------          ------
4951  GCGTAGAGGATCGAGATCTCGATCCCGCGAAATTAATACGACTCA CTATAGGGGAATTGTGAGCGGATAACAATTCCCCTCTAGAAATAA
      CGCATCTCCTAGCTCTAGAGCTAGGGCGCTTTAATTATGCTGAGT GATATCCCCTTAACACTCGCCTATTGTTAAGGGGAGATCTTTATT

+2                                    MetPheAsnLeuPro ProGlyAsnTyrLysLysProLysLeuLeuTyrCysSerAsnGl
                                                       SmaI                           PstI
                                                      ------                         ------
                        NdeI                      AvaI              HindIII            BfmI
                       ------                    ------             -------           ------
5041  TTTTGTTTAACTTTAAGAAGGAGATATACATATGTTTAACCTTCC GCCCGGGAATTACAAAAAAACCCAAGCTTCTTTACTGCAGTAACGG
      AAAACAAATTGAAATTCTTCCTCTATATGTATACAAATTGGAAGG CGGGCCCTTAATGTTTTTTGGGTTCGAAGAAATGACGTCATTGCC +2 yGlyHisPheLeuArgIleLeuProAspGlyThrValAspGlyThr ArgAspArgSerAspGlnHisIleGlnLeuGlnLeuSerAlaGl
                                                                     PvuI
                                                                    ------
               EcoRI                            NruI                     PvuII            XmaIII
              ------                           ------                   ------           ------
5131  AGGACACTTCCTGCGAATTCTGCCAGATGGCACAGTAGATGGGAC TCGCGATCGCTCCGACCAGCACATTCAGCTGCAACTCTCGGCCGA
      TCCTGTGAAGGACGCTTAAGACGGTCTACCGTGTCATCTACCCTG AGCGCTAGCGAGGCTGGTCGTGTAAGTCGACGTTGAGAGCCGGCT +2 uSerValGlyGluValTyrIleLysSerThrGluThrGlyGlnTyr LeuAlaMetAspThrAspGlyLeuLeuTyrGlySerGlnThrPr
                                       SalI
                                      ------
                    HindII            RsaI           StyI
                   ------            ------         ------
                    HincII   MlsI Csp6I     NcoI
                   ------   --------------  ------
5221  AAGCGTTGGAGAGGTCTATATCAAGTCGACGGAGACTGGCCAGTA CCTTGCCATGGACACCGATGGGCTTCTGTATGGCTCACAGACGCC
      TTCGCAACCTCTCCAGATATAGTTCAGCTGCCTCTGACCGGTCAT GGAACGGTACCTGTGGCTACCCGAAGACATACCGAGTGTCTGCGG +2 oAsnGluGluCysLeuPheLeuGluArgLeuGluGluAsnHisTyr AsnThrTyrIleSerLysLysHisAlaGluLysAsnTrpPheVa
                                                                RsaI
                                                                ----
           Mval2691       XbaI                                  Csp6I
          --------       ------                                ------
5311  TAACGAAGAATGCTTGTTTCTAGAAAGACTAGAAGAAAACCATTA CAACACGTACATATCGAAAAAACATGCAGAGAAGAACTGGTTTGT
      ATTGCTTCTTACGAACAAAGATCTTTCTGATCTTCTTTTGGTAAT GTTGTGCATGTATAGCTTTTTTGTACGTCTCTTCTTGACCAAACA +2 lGlyLeuLysLysAsnGlySerCysLysArgGlyProArgThrHis TyrGlyGlnLysAlaIleLeuPheLeuProLeuProValSerSe
                                                                                              SacI
                                                                                             ------
          StuI                                      MlsI                                     Ecl136II
         ------                                    ------                                    --------
5401  AGGCCTTAAAAAAAATGGTTCCTGTAAGCGTGGACCACGGACTCA CTATGGCCAAAAGGCTATCTTGTTCCTGCCACTACCAGTGAGCTC
      TCCGGAATTTTTTTTACCAAGGACATTCGCACCTGGTGCCTGAGT GATACCGGTTTTCCGATAGAACAAGGACGGTGATGGTCACTCGAG +2 rAsp***
                              SalI
                             ------
                 EcoRI SacI  HindII        XmaIII       XhoI
                ----- ----- ------        ------       ------
        BamHI    Ecl136IIHincIIHindIII NotI    AvaI
       ------   ----------------------- ----   ------
5491  CGACTAAGGATCCGAATTCGAGCTCCGTCGACAAGCTTGCGGCCG CACTCGAGCACCACCACCACCACCACTGAGATCCGGCTGCTAACA
      GCTGATTCCTAGGCTTAAGCTCGAGGCAGCTGTTCGAACGCCGGC GTGAGCTCGTGGTGGTGGTGGTGGTGACTCTAGGCCGACGATTGT
```

NUCLEOTIDE AND AMINO ACID SEQUENCE FOR CHEMICALLY SYNTHESIZED HUMAN A FGF (140 AMINO ACIDS)

FIG. 8

ELECTROPHOREGRAMM

1—MOLECULAR WEIGHT KIT (94 000,67 000,43 000,30 000 20 100, 14 4000)

THE CULTURAL MEDIUM, CONTAINING:
2—haFGF 134(40μ l OF THE CULTURAL MEDIUM)
3—haFGF 140(40μ l OF THE CULTURAL MEDIUM)
4—IFNα2B(40μ l OF THE CULTURAL MEDIUM)
5—haFGF 155(40μ l OF THE CULTURAL MEDIUM)
6—HGH(40μ l OF THE CULTURAL MEDIUM)
7—MAP(40μ l OF THE CULTURAL MEDIUM)
8—β—GALACTOSIDASE OF E. COLI(40μ l OF THE CULTURAL MEDIUM)

ELECTROPHOREGRAMM OF THE PURIEFIED PRODUCTS:

1—MOLECULAR WEIGHT KIT (94 000,67 000,43 000,30 000 20 100, 14 4000)
2—haFGF 134
3—haFGF 140
4—haFGF 146
5—IFNα2B
6—haFGF 155
7—MAP
8—MOLECULAR WEIGHT KIT

1ugm recombinant haFGF 155

CONTROL 10 pgHBGF 1 without HBGF 1

10 ug/kg HBGF-1 without HBGF-1

10 ug/kg HBGF-1

10 ug/kg HBGF-1

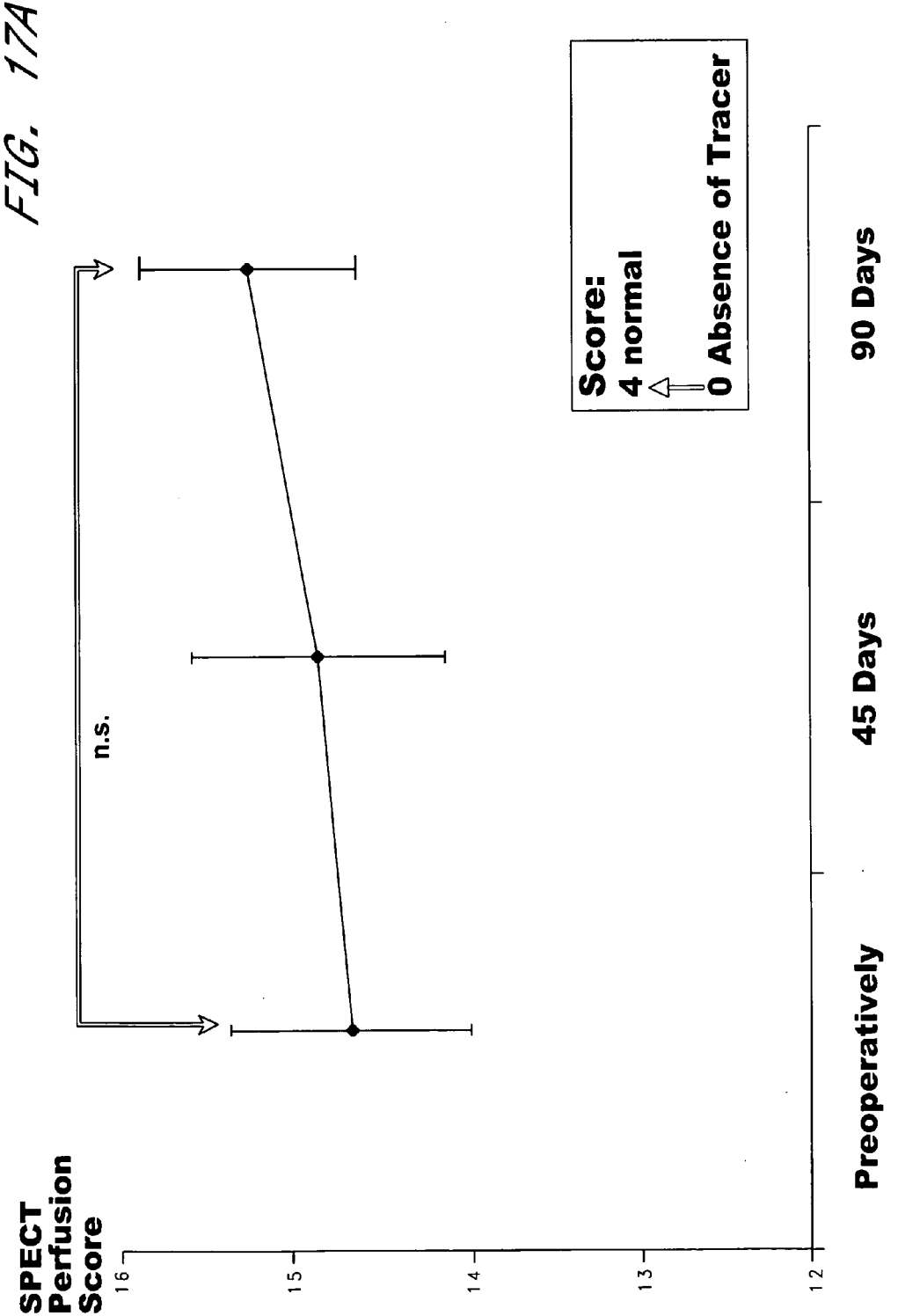

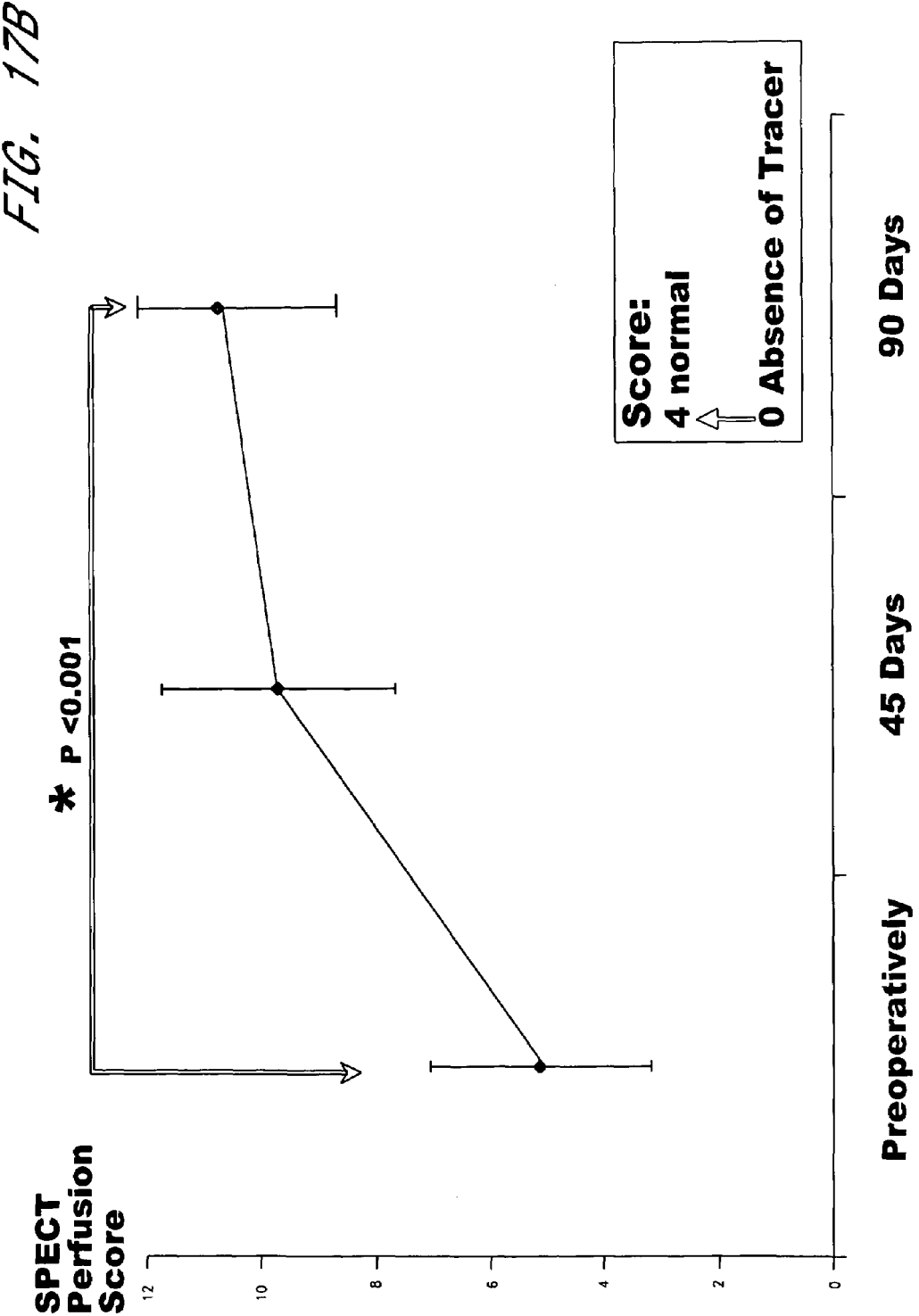

SEQUENCE LISTING

<160> NUMBER OF SEQ ID NOS: 8

<210> SEQ ID NO 1
<211> LENGTH: 630
<212> TYPE: DNA
<213> ORGANISM: Artificial Sequence
<220> FEATURE:
<223> OTHER INFORMATION: Chemically synthesized sequence for human acidic Fibroblast Growth Factor (155 amino acids) using preferred codons for E. coli
<220> FEATURE:
<221> NAME/KEY: CDS
<222> LOCATION: (122)...(590)

<400> SEQUENCE: 1

```
gcgtagagga tcgagatctc gatcccgcga aattaatacg actcactata ggggaattgt      60
gagcggataa caattcccct ctagaaataa ttttgtttaa ctttaagaag gagatataca     120 t atg gct gaa ggg gaa atc acc acc ttt aca gcg tta acg gag aaa ttt     169
  Met Ala Glu Gly Glu Ile Thr Thr Phe Thr Ala Leu Thr Glu Lys Phe
   1               5                  10                  15 aac ctt ccg ccc ggg aat tac aaa aaa ccc aag ctt ctt tac tgc agt      217
Asn Leu Pro Pro Gly Asn Tyr Lys Lys Pro Lys Leu Leu Tyr Cys Ser
                20                  25                  30 aac gga gga cac ttc ctg cga att ctg cca gat ggc aca gta gat ggg      265
Asn Gly Gly His Phe Leu Arg Ile Leu Pro Asp Gly Thr Val Asp Gly
         35                  40                  45 act cgc gat cgc tcc gac cag cac att cag ctg caa ctc tcg gcc gaa      313
Thr Arg Asp Arg Ser Asp Gln His Ile Gln Leu Gln Leu Ser Ala Glu
 50                  55                  60 agc gtt gga gag gtc tat atc aag tcg acg gag act ggc cag tac ctt      361
Ser Val Gly Glu Val Tyr Ile Lys Ser Thr Glu Thr Gly Gln Tyr Leu
 65                  70                  75                  80 gcc atg gac acc gat ggg ctt ctg tat ggc tca cag acg cct aac gaa      409
Ala Met Asp Thr Asp Gly Leu Leu Tyr Gly Ser Gln Thr Pro Asn Glu
                 85                  90                  95 gaa tgc ttg ttt cta gaa aga cta gaa gaa aac cat tac aac acg tac      457
Glu Cys Leu Phe Leu Glu Arg Leu Glu Glu Asn His Tyr Asn Thr Tyr
                100                 105                 110 ata tcg aaa aaa cat gca gag aag aac tgg ttt gta ggc ctt aaa aaa      505
Ile Ser Lys Lys His Ala Glu Lys Asn Trp Phe Val Gly Leu Lys Lys
        115                 120                 125 aat ggt tcc tgt aag cgt gga cca cgg act cac tat ggc caa aag gct      553
Asn Gly Ser Cys Lys Arg Gly Pro Arg Thr His Tyr Gly Gln Lys Ala
    130                 135                 140 atc ttg ttc ctg cca cta cca gtg agc tcc gac taa g gatccgaatt         600
Ile Leu Phe Leu Pro Leu Pro Val Ser Ser Asp *
145                 150                 155 cgagctccgt cgacaagctt gcggccgcac                                     630
```

<210> SEQ ID NO 2
<211> LENGTH: 155
<212> TYPE: PRT
<213> ORGANISM: Homo sapiens

<400> SEQUENCE: 2

```
Met Ala Glu Gly Glu Ile Thr Thr Phe Thr Ala Leu Thr Glu Lys Phe
1               5                   10                  15
Asn Leu Pro Pro Gly Asn Tyr Lys Lys Pro Lys Leu Leu Tyr Cys Ser
            20                  25                  30
Asn Gly Gly His Phe Leu Arg Ile Leu Pro Asp Gly Thr Val Asp Gly
        35                  40                  45
Thr Arg Asp Arg Ser Asp Gln His Ile Gln Leu Gln Leu Ser Ala Glu
    50                  55                  60
Ser Val Gly Glu Val Tyr Ile Lys Ser Thr Glu Thr Gly Gln Tyr Leu
65                  70                  75                  80
Ala Met Asp Thr Asp Gly Leu Leu Tyr Gly Ser Gln Thr Pro Asn Glu
                85                  90                  95
Glu Cys Leu Phe Leu Glu Arg Leu Glu Glu Asn His Tyr Asn Thr Tyr
            100                 105                 110
Ile Ser Lys Lys His Ala Glu Lys Asn Trp Phe Val Gly Leu Lys Lys
        115                 120                 125
Asn Gly Ser Cys Lys Arg Gly Pro Arg Thr His Tyr Gly Gln Lys Ala
    130                 135                 140
Ile Leu Phe Leu Pro Leu Pro Val Ser Ser Asp
145                 150                 155
```

<210> SEQ ID NO 3
<211> LENGTH: 468
<212> TYPE: DNA
<213> ORGANISM: Homo sapiens

<400> SEQUENCE: 3

```
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
aattggtttg ttggcctcaa gaagaatggg agctgcaaac gcggtcctcg gactcactat    420
ggccagaaag caatcttgtt tctccccctg ccagtctctt ctgattaa                 468
```

<210> SEQ ID NO 4
<211> LENGTH: 630
<212> TYPE: DNA
<213> ORGANISM: Artificial Sequence
<220> FEATURE:
<223> OTHER INFORMATION: Chemically synthesized sequence for human
                        acidic Fibroblast Growth Factor (134 amino
                        acids) using preferred codons for E. coli
<220> FEATURE:
<221> NAME/KEY: CDS
<222> LOCATION: (122)...(526)

<400> SEQUENCE: 4

```
gcgtagagga tcgagatctc gatcccgcga aattaatacg actcactata ggggaattgt      60
```

```
gagcggataa caattcccct ctagaaataa ttttgtttaa ctttaagaag gagatataca    120 t atg aat tac aaa aaa ccc aag ctt ctt tac tgc agt aac gga gga cac   169
  Met Asn Tyr Lys Lys Pro Lys Leu Leu Tyr Cys Ser Asn Gly Gly His
  1               5                   10                  15 ttc ctg cga att ctg cca gat ggc aca gta gat ggg act cgc gat cgc    217
Phe Leu Arg Ile Leu Pro Asp Gly Thr Val Asp Gly Thr Arg Asp Arg
                20                  25                  30 tcc gac cag cac att cag ctg caa ctc tcg gcc gaa agc gtt gga gag    265
Ser Asp Gln His Ile Gln Leu Gln Leu Ser Ala Glu Ser Val Gly Glu
        35                  40                  45 gtc tat atc aag tcg acg gag act ggc cag tac ctt gcc atg gac acc    313
Val Tyr Ile Lys Ser Thr Glu Thr Gly Gln Tyr Leu Ala Met Asp Thr
    50                  55                  60 gat ggg ctt ctg tat ggc tca cag acg cct aac gaa gaa tgc ttg ttt    361
Asp Gly Leu Leu Tyr Gly Ser Gln Thr Pro Asn Glu Glu Cys Leu Phe
65                  70                  75                  80 cta gaa aga cta gaa gaa aac cat tac aac acg tac ata tcg aaa aaa    409
Leu Glu Arg Leu Glu Glu Asn His Tyr Asn Thr Tyr Ile Ser Lys Lys
                85                  90                  95 cat gca gag aag aac tgg ttt gta ggc ctt aaa aaa aat ggt tcc tgt    457
His Ala Glu Lys Asn Trp Phe Val Gly Leu Lys Lys Asn Gly Ser Cys
            100                 105                 110 aag cgt gga cca cgg act cac tat ggc caa aag gct atc ttg ttc ctg    505
Lys Arg Gly Pro Arg Thr His Tyr Gly Gln Lys Ala Ile Leu Phe Leu
        115                 120                 125 cca cta cca gtg agc tcc gac taaggatccg aattcgagct ccgtcgacaa       556
Pro Leu Pro Val Ser Ser Asp
        130                 135 gcttgcggcc gcactcgagc accaccacca ccaccactga gatccggctg ctaacaaagc   616
ccgaaaggaa gctg                                                     630

<210> SEQ ID NO 5
<211> LENGTH: 135
<212> TYPE: PRT
<213> ORGANISM: Homo sapiens

<400> SEQUENCE: 5

Met Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
                20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
        130                 135

<210> SEQ ID NO 6
```

```
<211> LENGTH: 630
<212> TYPE: DNA
<213> ORGANISM: Artificial Sequence
<220> FEATURE:
<223> OTHER INFORMATION: Chemically synthesized sequence for human
                         acidic Fibroblast Growth Factor (140 amino
                         acids) using preferred codons for E. coli
<220> FEATURE:
<221> NAME/KEY: CDS
<222> LOCATION: (122)...(544)

<400> SEQUENCE: 6
gcgtagagga tcgagatctc gatcccgcga aattaatacg actcactata ggggaattgt      60
gagcggataa caattcccct ctagaaataa ttttgtttaa ctttaagaag gagatataca     120 t atg ttt aac ctt ccg ccc ggg aat tac aaa aaa ccc aag ctt ctt tac    169
  Met Phe Asn Leu Pro Pro Gly Asn Tyr Lys Lys Pro Lys Leu Leu Tyr
  1               5                   10                  15 tgc agt aac gga gga cac ttc ctg cga att ctg cca gat ggc aca gta       217
Cys Ser Asn Gly Gly His Phe Leu Arg Ile Leu Pro Asp Gly Thr Val
            20                  25                  30 gat ggg act cgc gat cgc tcc gac cag cac att cag ctg caa ctc tcg       265
Asp Gly Thr Arg Asp Arg Ser Asp Gln His Ile Gln Leu Gln Leu Ser
 35                  40                  45 gcc gaa agc gtt gga gag gtc tat atc aag tcg acg gag act ggc cag       313
Ala Glu Ser Val Gly Glu Val Tyr Ile Lys Ser Thr Glu Thr Gly Gln
 50                  55                  60 tac ctt gcc atg gac acc gat ggg ctt ctg tat ggc tca cag acg cct       361
Tyr Leu Ala Met Asp Thr Asp Gly Leu Leu Tyr Gly Ser Gln Thr Pro
 65                  70                  75                  80 aac gaa gaa tgc ttg ttt cta gaa aga cta gaa gaa aac cat tac aac       409
Asn Glu Glu Cys Leu Phe Leu Glu Arg Leu Glu Glu Asn His Tyr Asn
                 85                  90                  95 acg tac ata tcg aaa aaa cat gca gag aag aac tgg ttt gta ggc ctt       457
Thr Tyr Ile Ser Lys Lys His Ala Glu Lys Asn Trp Phe Val Gly Leu
            100                 105                 110 aaa aaa aat ggt tcc tgt aag cgt gga cca cgg act cac tat ggc caa       505
Lys Lys Asn Gly Ser Cys Lys Arg Gly Pro Arg Thr His Tyr Gly Gln
        115                 120                 125 aag gct atc ttg ttc ctg cca cta cca gtg agc tcc gac taaggatccg        554
Lys Ala Ile Leu Phe Leu Pro Leu Pro Val Ser Ser Asp
    130                 135                 140 aattcgagct ccgtcgacaa gcttgcggcc gcactcgagc accaccacca ccaccactga    614
gatccggctg ctaaca                                                     630

<210> SEQ ID NO 7
<211> LENGTH: 141
<212> TYPE: PRT
<213> ORGANISM: Homo sapiens

<400> SEQUENCE: 7

Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80
```

-continued

```
Asn Glu Glu Cys Leu Phe Leu Glu Arg Leu Glu Glu Asn His Tyr Asn
                 85                  90                  95
Thr Tyr Ile Ser Lys Lys His Ala Glu Lys Asn Trp Phe Val Gly Leu
            100                 105                 110
Lys Lys Asn Gly Ser Cys Lys Arg Gly Pro Arg Thr His Tyr Gly Gln
        115                 120                 125
Lys Ala Ile Leu Phe Leu Pro Leu Pro Val Ser Ser Asp
    130                 135                 140

<210> SEQ ID NO 8
<211> LENGTH: 154
<212> TYPE: PRT
<213> ORGANISM: Homo sapiens

<400> SEQUENCE: 8

Ala Glu Gly Glu Ile Thr Thr Phe Thr Ala Leu Thr Glu Lys Phe Asn
1               5                   10                  15
Leu Pro Pro Gly Asn Tyr Lys Lys Pro Lys Leu Leu Tyr Cys Ser Asn
            20                  25                  30
Gly Gly His Phe Leu Arg Ile Leu Pro Asp Gly Thr Val Asp Gly Thr
        35                  40                  45
Arg Asp Arg Ser Asp Gln His Ile Gln Leu Gln Leu Ser Ala Glu Ser
    50                  55                  60
Val Gly Glu Val Tyr Ile Lys Ser Thr Glu Thr Gly Gln Tyr Leu Ala
65                  70                  75                  80
Met Asp Thr Asp Gly Leu Leu Tyr Gly Ser Gln Thr Pro Asn Glu Glu
            85                  90                  95
Cys Leu Phe Leu Glu Arg Leu Glu Glu Asn His Tyr Asn Thr Tyr Ile
            100                 105                 110
Ser Lys Lys His Ala Glu Lys Asn Trp Phe Val Gly Leu Lys Lys Asn
        115                 120                 125
Gly Ser Cys Lys Arg Gly Pro Arg Thr His Tyr Gly Gln Lys Ala Ile
    130                 135                 140
Leu Phe Leu Pro Leu Pro Val Ser Ser Asp
145                 150
```

METHOD OF PRODUCING BIOLOGICALLY ACTIVE HUMAN ACIDIC FIBROBLAST GROWTH FACTOR AND ITS USE IN PROMOTING ANGIOGENESIS

RELATED APPLICATION

The present application is a continuation-in-part of U.S. application Ser. No. 09/929,945, filed Aug. 15, 2001 now U.S. Pat. No. 6,642,026 which claims priority to provisional patent application Ser. No. 60/225,406, filed on Aug. 15, 2000. This application is also a continuation-in-part of U.S. application Ser. No. 09/358,780, filed Jul. 22, 1999 now abandoned which claims priority to provisional patent application serial No. 60/093,962, filed Jul. 24, 1998. All of these applications are incorporated herein by reference.

BACKGROUND OF THE INVENTION

1. Field of the Invention

The field of the invention relates to methods of producing a recombinant fibroblast growth factor protein and its use in promoting angiogenesis.

2. Description of the Related Art

Fibroblast growth factors (FGF) are nine structurally related polypeptides, which are potent regulators of cell proliferation, differentiation and normal development. They also take part in pathological processes of tumorogenesis and metastasis (Galzie, et al. Biochem. Cell Biol. (1997) 75:669–685). They are potent mitogens and differentiation factors for a broad range of mesoderm and neuroectoderm derived cells, including endothelial cells.

The heparin proteoglycans, heparin or heparin sulfate, bind several FGF molecules together as a complex which are presented to the FGF receptors. FGF proteins bind to their receptors resulting in the activation of protein tyrosine kinases. The phosphorylation of these tyrosine kinases initiates multiple signals including the transcription of new mRNA's.

Two fibroblast growth factors, basic and acidic, are described as potent inducers of angiogenesis (Friesel et al. (1995) FASEB J. 9:919–925). Both basic and acidic factors have been implicated in the control of blood vessel formation and their involvement in normal and pathological angiogenesis (Slavin, J. (1995) Cell Biology International 19(5): 431–444). These factors have been purified, their amino acid sequences have been determined and their cDNA has been cloned and sequenced.

Acidic Fibroblast Growth Factor (aFGF) has been described under various names including embryonic kidney-derived angiogenesis factor I, astroglial growth factor I, endothelial cell growth factor (ECGF), retina-derived growth factor, heparin-binding growth factor class 1, endothelial growth factor, eye-derived growth factor II, prostatropin, and glial maturation factor (Gospodarowicz, et al. (1987) Journal of Cellular Physiology supplement 5: 15–26). Cloning, nucleotide sequence and chromosome localization have been described (Jaye et al. (1986) Science 233:541–545).

Acidic fibroblast growth factor (aFGF or FGF-1) belongs to a large family of heparin-binding growth factors that are now generally referred to as fibroblast growth factors (FGFs). To date there are at least 22 known members of the FGF family, with FGF-1 and FGF-2 (basic FGF, bFGF) as its prototype members. Besides vascular endothelial growth factor (VEGF), FGF-1 is well known as a highly potent angiogenic agent with mitogenic activity for a wide variety of different cell types as well in tissue culture as in vivo. The biological process of angiogenesis is initiated by binding of FGF-1 to the specific receptor molecules (FGFR) located on the cell surface. FGFR activation is followed by tyrosine autophosphorylation—thus initiating the complex cascade of matrix dissolution, cell differentiation and proliferation, finally resulting in tube formation and new vessel growth.

The aFGF gene is situated on chromosome 5. It has a single copy and encodes three exons separated by two introns. A 4.8 kb mRNA translates synthesis of a form of aFGF with 155 amino acids. However, the N-terminal methionine residue is removed in vivo to give a 154 amino acid form. This 154 amino acid form of the aFGF is processed into two forms which are 140 and 134 amino acids. The aFGF protein is an anionic mitogen of molecular weight 15,000–17,000 D.

The aFGF protein has been found in brain, retina, bone matrix and osteosarcoma. Only forms with 140 and 134 amino acids have been obtained from tissues. It has been suggested that the truncated aFGF forms are an artifact created by specific proteases during aFGF extraction and isolation (Gospodarowicz, et al. (1987) Journal of Cellular Physiology supplement 5:15–26; Jaye et al. (1987) The Journal of Biological Chemistry 262 (34):16612–16617).

It has been suggested that heparin potentiates the biological activity of the aFGF protein (Thornton et al. (1983) Science 222 (4624): 623–625). Heparin binding to aFGF has been observed (Maciag et al. (1984) Science 225 (4665): 932–935). This heparin-binding characteristic has been used as an efficient affinity chromatography method for the purification of aFGF protein. Heparin potentiates the biological activity of aFGF and the enhanced activity of the aFGF-heparin complex varies from several to one hundred fold (Lobb, et al. (1986) Anal. Biochem. 154:1–14).

In one embodiment, the present invention is related to the treatment of coronary heart disease by revascularization therapy, and more particularly to pharmaceutical compositions containing recombinant fibroblast growth factor, procedures for preparing recombinant fibroblast growth factor, and methods for delivering the pharmaceutical compositions containing a fibroblast growth factor to the ischemic myocardium.

Heart attack, or myocardial infarction, due to coronary heart disease (CHD) is the single leading cause of death in the U.S. according to the American Heart Association. Myocardial infarction occurs when the blood supply to part of the heart muscle, or myocardium, is severely reduced or stopped, thereby depriving the myocardium of oxygen. This oxygen deprivation, or ischemia, occurs when one of the coronary arteries which supply blood to the myocardium is blocked. The blockage, or stenosis, most frequently results from atherosclerosis, a condition associated with the buildup of fatty deposits in the vessel walls. Statistics based upon the National Heart, Lung, and Blood Institute's Atherosclerotic Risk in Communities (ARIC) Study (1987–1994) and the Framingham Heart Study, indicate that the CHD-related mortality rate in the U.S. is one of every 4.8 deaths (481,287 deaths in 1995). Over one million new and recurrent cases of heart attack and almost 14 million victims of myocardial ischemia, angina and other manifestations of CHD (7.1 million men and 6.8 million women) are reported each year. Moreover, as many as 3 to 4 million individuals in the U.S. alone may have ischemic episodes (silent ischemia) without knowing it.

Procedures currently available for treating CHD and myocardial ischemia include: 1) coronary artery bypass graft, wherein a segment of a vein is harvested from the patient's leg and grafted in such a manner as to reroute blood around the stenosis; 2) percutaneous transluminal coronary angioplasty, or balloon angioplasty, wherein a catheter having a deflated balloon is passed into the stenosed region of the artery and the balloon is then inflated to widen the vessel lumen; 3) laser angioplasty, wherein a catheter having a laser at its distal tip is used to ablate the atherosclerotic plaque; 4) artherectomy, wherein a high-speed rotating 'burr' at the end of a catheter is used to grind away the atherosclerotic plaque; and 5) transmyocardial revascularization, in which a series of channels are cut in the myocardium by laser to allow blood from inside the left ventricle to permeate into the ischemic heart muscle. While variations, combinations and improvements in these basic approaches are constantly being developed, each of these alternative methods have significant disadvantages.

Thoracic surgeons performed approximately 573,000 bypass operations in 1995 in the U.S. alone. While coronary artery bypass has the advantage of creating a new path through which blood may flow freely to the myocardium, often by graft directly from the aorta or internal mammary artery, it also has the major disadvantage of requiring highly invasive open heart surgery. Indeed, the heart is generally stopped in bypass surgery to facilitate anastomosis of the graft to the coronary artery. Oxygenation and circulation are maintained by a heart-lung machine. Consequently, bypass patients face increased risk of damage to the kidneys, brain and other organs. In addition to the medical risks, bypass procedures are very expensive and require significant recovery time. Moreover, for many patients who are at high risk for major invasive surgery or who have advanced stage and/or diffuse CHD, coronary artery bypass procedures are not a viable option. Consequently, these patients must seek alternative treatments.

The most frequently utilized, less invasive alternative to bypass surgery, is percutaneous transluminal coronary angioplasty, commonly referred to as balloon angioplasty. Approximately 434,000 balloon angioplasties were performed in the U.S. in 1995. While such procedures are considerably less invasive and less expensive than coronary bypass surgery, the improvement in blood flow to the myocardium may be small and short-lived For instance, according to the American Heart Association, an increase in luminal diameter of greater than 20% is considered successful. Furthermore, restenosis occurs within six months in about 25–30% of patients who have undergone successful angioplasty. To reduce the incidence of restenosis following angioplasty, expandable structural supports, referred to as stents, may be deployed during angioplasty to maintain vessel diameter and blood flow. However, the endothelial and smooth muscle cells which comprise the vessel walls tend to infiltrate the stent scaffolding, eventually compromising blood flow. Finally, balloon angioplasty is not recommended for patients with severe diffuse CHD or in patients having greater than 50% occlusion in their left anterior descending (LAD) coronary artery. Thus, balloon angioplasty is neither sufficiently effective nor widely applicable to alleviate the debilitating symptoms of severe myocardial ischemia in many patients.

Two other catheter-based techniques, laser angioplasty and arthrectomy, are directed toward increased blood flow through removal of atherosclerotic plaque. While these techniques may be used alone, they are often used in conjunction with balloon angioplasty to increase luminal diameter. Unfortunately, plaque removed by these methods may generate debris and/or flaps which may cause sudden, dangerous post-operative occlusions.

Transmyocardial revascularization, or laser revascularization, is another procedure, which is both less invasive and less costly than bypass surgery, and has been forwarded as an option for those patients who are at high risk for a second bypass or angioplasty. By providing direct access of the ischemic myocardium to blood within the ventricular chamber, laser revascularization may be useful in treating patients whose coronary artery blockages are too diffuse to be treated effectively with site-directed bypass surgery and/or angioplasty. Unfortunately, the theoretical benefits of laser revascularization have yet to be proven safe and effective over time. Indeed, the generation of an array of channels cut through the walls of the heart by laser vaporization may serve merely as a stop-gap measure to address acute myocardial ischemia, while diminishing the long-term prognosis.

Thus, there remains a substantial gap in treatment options for CHD patients, particularly those who are at high risk for bypass surgery. Indeed, there is a need for a treatment protocol which is less invasive and less expensive than bypass surgery, and more effective than balloon angioplasty and transmyocardial revascularization.

Normal capillaries have a cell population with a low turnover rate of months or years. On occasion, however, a high turnover rate of this cell population is possible even under physiological conditions, and this naturally leads to the rapid growth of new capillaries and other blood vessels. Such a physiological process occurs in the development of the placenta, in fetal growth, and in wound healing, as well as in the formation of collaterals in response to tissue ischemia. Angiogenic polypeptide growth factors are essential for such processes as capillary growth or neoangiogenesis. These growth factors bring about their effects by significantly increasing cell proliferation, differentiation, and migration via high-affinity receptors on the surfaces of the endothelial cells. Accordingly, the present invention is directed toward revascularization of the myocardium via local-acting, growth factor-stimulated neoangiogenesis.

SUMMARY OF THE INVENTION

In one embodiment, the present invention relates to a method for revascularizing an ischemic region, which includes the steps of preparing a pharmaceutical composition which includes a recombinant fibroblast growth factor-1 (FGF-1); and injecting an amount of the pharmaceutical composition into the ischemic region, the amount being sufficient to induce local neoangiogenesis. The FGF-1 is prepared by a process which includes the steps of:
(i) transforming an *E. coli* host cell with a plasmid which includes an expressible gene encoding a biologically active human acidic fibroblast growth factor protein, operably linked to a promoter;
(ii) infecting the transformed bacterial host cell with a bacteriophage λ which mediates delayed lysis; and
(iii) cultivating the *E. coli* host cell under a culture condition that induces lytic growth of the cell without lysis until a desired level of production of the protein is reached, where the protein is produced as a soluble, biologically-active human acidic fibroblast growth factor protein.

In a preferred embodiment, the expressible gene has a sequence contained within the group including SEQ ID NO: 1, SEQ ID NO: 3, SEQ ID NO: 4, and SEQ ID NO: 6.

In a preferred embodiment, the bacteriophage λ has a temperature-sensitive mutation which is $cI_{857}$. In a preferred embodiment, the *E. coli* host cells are grown at a temperature between 20 to 37° C. prior to the cultivating step which prevents lytic growth of the bacteriophage λ. In a preferred embodiment, the bacteriophage λ has a mutation in at least one gene which mediates delayed lysis. In a more preferred embodiment, the at least one gene which mediates delayed lysis is selected from a group which includes N, Q and R.

In some embodiments, the *E. coli* host cell produces a suppressor for the repair of amber-mutations. In alternate embodiments, the *E. coli* host cell lacks a suppressor for the repair of amber-mutations. In a preferred embodiment, the infecting bacteriophage λ is provided at a multiplicity of infection in a range of about 1 to about 100. In a more preferred embodiment, the infecting bacteriophage λ is provided at a multiplicity of infection in a range of about 10 to about 25. Preferably, bacteriophage-mediated delayed lysis of the *E. coli* host cell is delayed at higher multiplicities of infection relative to lower multiplicities of infection.

In a preferred embodiment, the promoter is a T7 polymerase promoter and the *E. coli* host cell includes a gene for T7 RNA polymerase. In a more preferred embodiment, the gene for T7 RNA polymerase gene is under the control of an inducible promoter. In a most preferred embodiment, the inducible promoter is a lac UV 5 promoter.

In a preferred embodiment, the biologically active human acidic fibroblast growth factor protein contains amino acids 9–155 as shown in SEQ ID NO: 2. In another preferred embodiment, the biologically active human acidic fibroblast growth factor protein contains amino acids 2–135 as shown in SEQ ID NO: 5. In a more preferred embodiment, the human acidic fibroblast growth factor protein has the sequence as set forth in SEQ ID NO: 7. In a most preferred embodiment, the biologically active human acidic fibroblast growth factor protein contains amino acids 2–141 as shown in SEQ ID NO: 7. In another preferred embodiment, the the biologically active human acidic fibroblast growth factor protein includes the sequence of SEQ ID NO: 8.

In a preferred embodiment, FGF-1 is injected at a final concentration in a range of about 0.1 µg/kg body weight per site to about 10 mg/kg body weight per site. In a more preferred embodiment, FGF-1 is injected at a final concentration in a range of about 10 to 100 µg/kg body weight per site.

In some preferred embodiments, the pharmaceutical composition further includes a physiologic glue. Preferably, the physiologic glue is fibrin glue. Preferably, the FGF-1 and the physiologic glue are mixed immediately prior to application. In an alternate embodiment, the method of revascularizing an ischemic region further includes the step of injecting a composition including a physiologic glue subsequent to injection with the pharmaceutical composition containing the FGF-1.

In some embodiments, the pharmaceutical composition further includes an anticoagulant. Preferably, the anticoagulant is heparin. In a preferred embodiment, the heparin is applied at a final concentration in a range of about 1 U per ml to about 1000 U per ml.

In a preferred embodiment, the injecting step further includes the steps of:
making a thoracotomy incision;
identifying the at least one site of coronary artery stenosis;
administering a β-blocker to reduce the heart rate to a range of about 20–60 beats per minute; and
injecting the pharmaceutical composition intramyocardially at or near the at least one site of coronary artery stenosis.

In a preferred embodiment, the thoracotomy incision further includes an anterior left-sided incision; dissecting a region of costal cartilage over a $5^{th}$ rib; and opening a left pleural space and a pericardium. In a preferred embodiment, the step of identifying the at least one site of coronary artery stenosis further includes retracting the heart forward using traction sutures. In a preferred embodiment, the method further includes a coronary artery bypass graft.

Preferably, the neoangiogenesis is long term and occurs in the ischemic region at 6 weeks after the injection. More preferably, the neoangiogenesis is long term and occurs in the ischemic region at 3 months after the injection.

In another aspect the invention relates to a method for treating coronary artery disease in a patient which includes the steps of preparing a pharmaceutical composition which includes a recombinant fibroblast growth factor-1 (FGF-1); injecting an amount of the pharmaceutical composition into at least one site in a heart wall, the amount being sufficient to improve myocardial perfusion; and injecting a composition which includes a physiological glue to a surface of the heart at the site(s) where the pharmaceutical composition was injected, wherein the FGF-1 is prepared by a process which includes the steps of:
(i) transforming an *E. coli* host cell with a plasmid which includes an expressible gene encoding a biologically active human acidic fibroblast growth factor protein, operably linked to a promoter;
(ii) infecting the transformed bacterial host cell with a bacteriophage λ which mediates delayed lysis; and
(iii) cultivating the *E. coli* host cell under a culture condition that induces lytic growth of the cell without lysis until a desired level of production of the protein is reached, wherein the protein is produced as a soluble, biologically-active human acidic fibroblast growth factor protein.

Preferably, the physiologic glue is fibrin glue.

In a preferred embodiment, the expressible gene has a sequence contained within the group including SEQ ID NO: 1, SEQ ID NO: 3, SEQ ID NO: 4, and SEQ ID NO: 6.

In a preferred embodiment, the bacteriophage λ has a temperature-sensitive mutation which is $cI_{857}$. In a preferred embodiment, the *E. coli* host cells are grown at a temperature between 20 to 37° C. prior to the cultivating step which prevents lytic growth of the bacteriophage λ. In a preferred embodiment, the bacteriophage λ has a mutation in at least one gene which mediates delayed lysis. In a more preferred embodiment, the at least one gene which mediates delayed lysis is selected from a group which includes N, Q and R.

In some embodiments, the *E. coli* host cell produces a suppressor for the repair of amber-mutations. In alternate embodiments, the *E. coli* host cell lacks a suppressor for the repair of amber-mutations. In a preferred embodiment, the infecting bacteriophage λ is provided at a multiplicity of infection in a range of about 1 to about 100. In a more preferred embodiment, the infecting bacteriophage λ is provided at a multiplicity of infection in a range of about 10 to about 25. Preferably, bacteriophage-mediated delayed lysis of the *E. coli* host cell is delayed at higher multiplicities of infection relative to lower multiplicities of infection.

In a preferred embodiment, the promoter is a T7 polymerase promoter and the *E. coli* host cell includes a gene for T7 RNA polymerase. In a more preferred embodiment, the gene for T7 RNA polymerase gene is under the control of an inducible promoter. In a most preferred embodiment, the inducible promoter is a lac UV 5 promoter.

In a preferred embodiment, the biologically active human acidic fibroblast growth factor protein contains amino acids 9–155 as shown in SEQ ID NO: 2. In another preferred embodiment, the biologically active human acidic fibroblast growth factor protein contains amino acids 2–135 as shown in SEQ ID NO: 5. In a more preferred embodiment, the human acidic fibroblast growth factor protein has the sequence as set forth in SEQ ID NO: 7. In a most preferred embodiment, the biologically active human acidic fibroblast growth factor protein contains amino acids 2–141 as shown in SEQ ID NO: 7. In another preferred embodiment, the the biologically active human acidic fibroblast growth factor protein includes the sequence of SEQ ID NO: 8.

In a preferred embodiment, FGF-1 is injected at a final concentration in a range of about 0.1 μg/kg body weight per site to about 10 mg/kg body weight per site. In a more preferred embodiment, FGF-1 is injected at a final concentration in a range of about 10 to 100 μg/kg body weight per site.

In some embodiments, the pharmaceutical composition further includes an anticoagulant. Preferably, the anticoagulant is heparin. In a preferred embodiment, the heparin is applied at a final concentration in a range of about 1 U per ml to about 1000 U per ml.

In a preferred embodiment, the injecting step further includes the steps of:
making a thoracotomy incision;
identifying the at least one site of coronary artery stenosis;
administering a β-blocker to reduce the heart rate to a range of about 20–60 beats per minute; and
injecting the pharmaceutical composition intramyocardially at or near the at least one site of coronary artery stenosis.

In a preferred embodiment, the thoracotomy incision further includes an anterior left-sided incision; dissecting a region of costal cartilage over a $5^{th}$ rib; and opening a left pleural space and a pericardium. In a preferred embodiment, the step of identifying the at least one site of coronary artery stenosis further includes retracting the heart forward using traction sutures. In a preferred embodiment, the method further includes a coronary artery bypass graft.

Preferably, the neoangiogenesis is long term and occurs in the ischemic region at 6 weeks after the injection. More preferably, the neoangiogenesis is long term and occurs in the ischemic region at 3 months after the injection.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1 shows the chemically synthesized nucleotide sequence for human acidic fibroblast growth factor (155 amino acids) (SEQ ID NO: 1) which has been modified by substitution of naturally occurring codons with codons found in highly expressed E. coli proteins and the translated amino acid sequence (SEQ ID NO: 2).

FIG. 2 shows the modifications made in the chemically synthesized haFGF 155 codons. FGF fr HUMECGFB is the sequence obtained from GenBank (at NCBI) (SEQ ID NO: 3). HaFGF 155 is the chemically synthesized sequence of the present invention (SEQ ID NO: 1).

FIG. 6 shows the chemically synthesized nucleotide sequence for human acidic fibroblast growth factor (134 amino acids) (SEQ ID NO: 4) which has been modified by substitution of naturally occurring codons with codons found in highly expressed E. coli proteins and the translated amino acid sequence (SEQ ID NO: 5).

FIG. 8 shows the chemically synthesized nucleotide sequence for human acidic fibroblast growth factor (140 amino acids) (SEQ ID NO: 6) which has been modified by substitution of naturally occurring codons with codons found in highly expressed E. coli proteins and the translated amino acid sequence (SEQ ID NO: 7).

FIG. 11. Chicken embryo CAM blood vessels on the $14^{th}$ day of development after FGF treatment. Formation of chicken egg CAM new blood vessels on the $4^{th}$ day after application of the 154 amino acid form of the haFGF protein. Magnification 3×.

FIG. 17A shows summed Rest Score (SRS) of sestamibi scans for all study patients. Score: 0—no perfusion, 4—normal perfusion. A score of 16 represents the highest possible score per investigation. FIG. 17B shows summed Stress Score (SSS) of sestamibi scans for all study patients. Score: 0—no perfusion, 4—normal perfusion. A score of 16 represents the highest possible score per investigation.

DETAILED DESCRIPTION OF THE PREFERRED EMBODIMENTS

Figure 3:
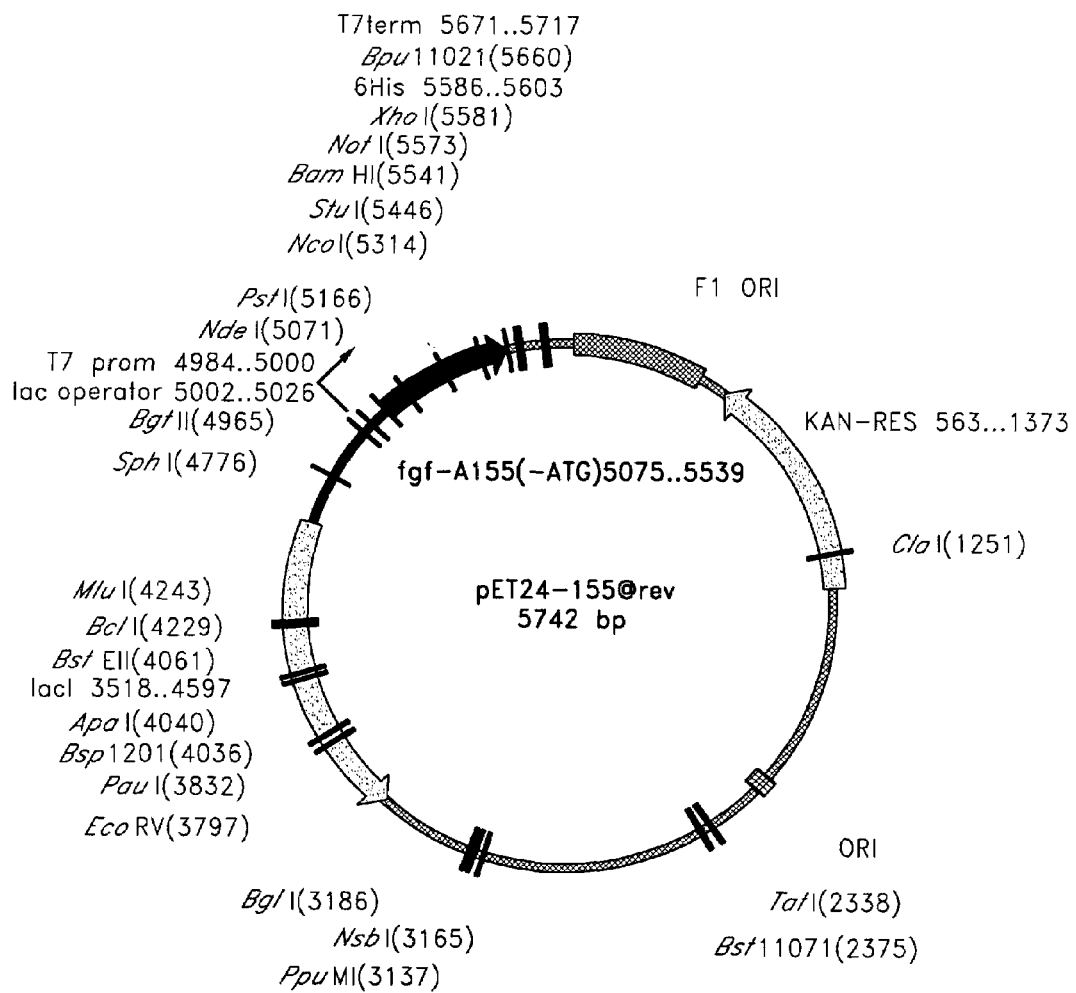
FIG. 3 shows the pET24-155@rev construct which contains the chemically synthesized haFGF 155 gene (SEQ ID NO: 1).

While the described embodiment represents the preferred embodiment of the present invention, it is to be understood that modifications will occur to those skilled in the art without departing from the spirit of the invention. The scope of the invention is therefore to be determined solely by the appended claims.

The haFGF155 gene encodes a protein containing 155 amino acid residues (SEQ ID NOS: 1 & 2). The first amino acid of the haFGF 155 sequence is the initiator methionine residue, which under normal situations would be removed during protein synthesis resulting in an FGF protein of 154 amino acids (SEQ ID NO: 8). However, it has only been possible to isolate two shorter aFGF forms from tissue samples. The two isolated forms contain 140 and 134 amino acid residues. The aFGF form containing 140 amino acids is considered complete, while the aFGF form containing 134 amino acids is considered to be truncated. It has not been possible to extract the aFGF form containing 155 or 154 amino acids from tissue samples. It is not known whether the shorter isoforms occur as a normal function of cell processing or as an artefact produced during the isolation procedure by specific proteases in the process of aFGF extraction. Western Blot analysis of the protein produced from the isolated DNA recombinant molecules for the three aFGF forms showed high expression of the 140 and 134 forms and a low expression level of the 154 form.

In a preferred embodiment of the present invention, the gene for human acidic fibroblast growth factor encodes the 154 amino acid form of the aFGF protein and is chemically synthesized (SEQ ID NO: 1). The nucleotide sequence of the haFGF 155 gene has been deduced on the basis of the previously described haFGF 155 amino acid sequence (SEQ ID NO: 2). The amino acid sequence of the synthesized haFGF155 gene does not differ from those previously described such as the translated sequence of the human aFGF nucleotide sequence of SEQ ID NO: 3 obtained from GenBank. However, the preferred nucleotide sequence of haFGF gene differs from those previously described. In a preferred embodiment of the present invention, the haFGF 155 gene has been chemically synthesized using the codons which are most often used by *E. coli* for intensively synthesized bacterial proteins. Preferred codon usage tables for *E. coli* are well known and available. Chemical synthesis of polynucleotides was carried out using well known methodology (Edge et al. (1983) Nucleic Acids Research 11 (18): 6419–6435).

Alternatively, other well known forms of the haFGF gene could be used by those skilled in the art in the practice of the present invention including isolated DNA from animal tissues encoding other forms of the haFGF protein known to those skilled in the art including the 154, the 146, the 140 and 134 isoforms and any variants, derivatives, analogs or fragments thereof. The human aFGF proteins may be used in methods to stimulate angiogenesis. Human aFGF produced by the practice of the claimed invention may also be used in a composition with a suitable pharmaceutical carrier. Such carriers include, but are not limited to, saline, buffered saline, water, dextrose and combinations thereof. In a preferred embodiment, a fibrin glue such as Tissucal™ (Baxter International, Duarte, Calif.) is used as carrier.

FIG. 1 shows the complete nucleotide sequence of the haFGF 155 gene, as synthesized by the present inventors (SEQ ID NO: 1). A sequence for human acidic fibroblast growth factor from GenBank (SEQ ID NO: 3) was compared to the chemically synthesized sequence of FIG. 1. The comparison is shown in FIG. 2. There are distinctions in 80 codons.

Expression and cloning vectors typically contain a promoter that is recognized by the host organism and is operably linked to the haFGF nucleic acid. Promoters are untranslated sequences located upstream (5') to the start codon of a structural gene (generally within 100–1000 base pairs) that control the transcription and translation of particular nucleic acid sequences, such as the haFGF nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by prokaryotic host cells are known. These promoters are operably linked to haFGF-encoding DNA by removing the promoter from the source DNA by restriction enzyme digestion and inserting the isolated promoter sequence into the vector.

Promoters known to those skilled in the art include β-lactamase and lactose promoter systems (Chang et al. (1978) Nature 275: 615; Goeddel et al. Nature (1979) 281: 544), alkaline phosphatase, and a tryptophan (trp) promoter system (Goeddel (1980) Nucleic Acids Research 8: 4057; Ep36,776). However, other known bacterial promoters are suitable. A most preferred promoter is the T7 promoter system. One skilled in the art would know how to ligate them to haFGF DNA using suitable linkers or adaptors to provide appropriate restriction sites. Promoters may also be used in tandem to achieve higher levels of expression.

Any number of prokaryote host cells are suitable for expressing the haFGF gene cloned into the vectors described herein. Preferred prokaryotic hosts include eubacteria such as Gram-negative or Gram-positive organisms, for example, Enterbacteriaceae such as *Escherichia*. A most preferred prokaryote host is *E. coli*.

Transformation means introducing DNA into an organism so that the DNA is capable of replication, either as an extrachromosomal element or by integration into the chromosome. Transformation of prokaryotic cells is performed using techniques well known to those skilled in the art such as treatment with $CaCl_2$ or electroporation.

An important advantage of infecting producer cells with a bacteriophage is that the phage causes a profound rearrangement of all macromolecular synthesis in the bacterial host cells. By turning off transcription of bacterial genes, phages may increase the copying of the targeted gene, and consequently, increase the output of desired product.

In one embodiment of the present super-production system, phage λ with amber-mutations that delay bacterial lysis (e.g., $Q^-$ and $R^-$ mutations) are provided in a strain of *E. coli*, designated $Su^o$, which lacks the suppressor responsible for correcting amber-mutations in phage λ. In order to obtain a non-suppressing ($Su^o$) strain of *E. coli*, $Su^o$ clones are selected from the wild-type $Su^+$ population. Preferably, a selection marker is inserted into the phage DNA, e.g., tetracycline or ampicillin resistance.

Selection of non-suppressing ($Su^o$) strains of *E. coli*, for example, *E. coli* K 802 was carried out with phage λ $cI_{857}$ $N_{am7}N_{am53}$ bla tet (hereinafter λ bla N'). Strain *E. coli* C600 (λ bla N') served as source of the phage. This phage was obtained by insertion of plasmid pCV 11 (bla tet) at EcoRI site into single-site (EcoRI) vector carrying ts-mutation in repressor gene ($cI_{857}$). Then two amber-mutations were introduced into the phage N gene by recombination in vivo.

Clones were tested for non-lysogenicity with phage λ clear. In addition to phage λ bla N', phage λ $cI_{857}$ $Q_{am117}$ $R_{am54}$ was used to check for suppressor.

As is known, phage λ N' mutant is not able to lyse the host cells and is present in cells in the form of extremely unstable plasmids. If the host cells contain suppressor, the amber-mutation is phenotypically corrected, the N protein is synthesized and the phage can develop lytically. This difference in the viability of $Su^+$ and $Su^o$ cells, infected by λ N', is used as a basis for selection of spontaneously appearing $Su^o$ revertants from the *E. coli* $Su^+$ cell population. Phage λ with an inserted plasmid that introduced the ampicillin and tetracycline resistance markers into cells was used to prevent the nonlysing $Su^o$ cells from masking the search for mutants. The phage also contains ts-mutation in the repressor gene that permits lytic development of such phage resulting in cell lysis.

If the medium supplemented with ampicillin and tetracycline is inoculated with $Su^+$ culture after its infection with phage λ bla N' with subsequent growth at 43° C., single suppressor-free cells containing phage λ bla N' in the form of plasmids must develop on plates. Curing the cells from the phage, we must obtain $Su^+$ derivatives of the parent cultures. The method can be subdivided into several stages.

Infection of Culture with Phage λ bla N'

The culture *E. coli* $Su^+$ was grown on the M9 medium with maltose at 37° C. under intense agitation to a density of $1-2 \times 10^8$ cells/ml. The cells were infected with phage λ bla N' at a multiplicity of 5–10 particles per cell and incubated for 20 min at 20° C. Under given conditions, the infection efficiency is about 100%, in addition to the bulk of $Su^+$ cells, the phage also infects single $Su^o$ cells.

Selection of Suppressor-Free Cells Containing Marker Phage

After infection, cells were plated out on agar medium supplemented with 12 γ/ml tetracycline and 20 γ/ml ampicillin and grown at 43° C. In 24 h, single colonies developed, which were replated on agar medium with antibiotics and grown at 37° C.

Curing of the Selected Clones from Phage λ bla N'

Since phage λ N' in the *E. coli* $Su^o$ cells is in the form of extremely unstable plasmids, in order to cure from the phage the selected clones were plated on selective agar medium without antibiotics and grown at 37° C. The number of cells that had lost the phage in the first passage on the medium without antibiotics amounted to 12–35%. The selection of such cells was carried out by monitoring the loss of antibiotic resistance and the acquisition of sensitivity to phage λ clear.

Testing of Cells for Repressor

The ability of phage λ with amber-mutations to form plaques on lawns of cured clones was checked. Isogenic suppressor-free derivatives of the parent *E. coli* Su+ strains are clones, on which phage λ bla N' did not form plaques, phage λ $cI_{857}$ $Q_{am117}$ $R_{am54}$ produced $1-3 \times 10^5$ PFU/ml, and phage λ $cI_{857}$ without mutations in genes Q and R produced $1 \times 10^{10}$ PFU/ml.

Using this method, we obtained $Su^o$ revertants of *E. coli* K 802 Su+. Based on the cell number at the moment of infection and the number of $Su^o$ revertants among them, the frequency of occurrence of suppressor-free cells was $3 \times 10^{-7}$.

In a preferred embodiment, the gene of interest is cloned into pET-24a(+) under the control of the T7 promoter. Preferred genes include, but are not limited to, genes encoding human aFGF 134 amino acid form, human aFGF 140 amino acid form, and human aFGF 146 amino acid form and human aFGF 155 amino acid form. In an alternate embodiment, the gene of interest may be cloned into both a bacterial plasmid and the λ phage under the control of appropriate promoters. In a most preferred embodiment, chemically synthesized haFGF 155 gene (SEQ ID NO: 1) is cloned into pET-24a(+) under the control of the T7 promoter.

The T7 promoter is recognized only by T7 RNA polymerase and is not recognized by the RNA polymerase of *E. coli*. The obtained plasmid with an haFGF gene was transformed into *E. coli* BL21(DE3). This strain contains the T7 RNA polymerase gene. The T7 RNA polymerase gene is under the control of the inducible lac UV5 promoter in order to induce T7 RNA polymerase synthesis only when necessary as this protein is toxic for the *E. coli* cell. The induction of the lac promoter is carried out by adding IPTG to the nutrient medium. In order to obtain a haFGF protein, the producer strain, containing the recombinant plasmid with the haFGF gene, is cultured under conditions of intensive aeration to a cell density of $5 \times 10^7 - 5 \times 10^9$ cells in 1 ml at a temperature of 20–40° C. Then it infected by lambda phage with the ts-mutation cI repressor gene with a multiplicity from 0.1 to 100 phage bodies per cell and incubation is continued at 20–37° C. for 2–14 hours. Simultaneously with the phage, IPTG at a concentration of 1 mM is introduced.

Production of the haFGF proteins was achieved by cultivation of the producer strain under conditions which slow down the lytic development of the lambda phage Such conditions include lowered temperature of cultivation and use of amber mutations in late lambda phage genes such as Q and R genes.

The haFGF proteins accumulated in the culture medium as a soluble proteins as a result of the producer strain cells lysis by lambda phage. The output of each haFGF protein generally constituted 20% of the soluble proteins accumulated in the culture medium. Debris was removed from the culture medium by centrifugation. The haFGF can then be purified from contaminant soluble proteins and polypeptides with the following procedures, which are exemplary of suitable purification procedures: by fractionation on an ion-exchange column; ethanol precipitation, reverse phase HPLC; chromatography on silica; immunoaffinity; SDS-PAGE; ammonium sulfate precipitation; and gel filtration. In one embodiment, the haFGF recombinant protein was purified using a C18 HPLC column. In another embodiment, the haFGF recombinant proteins were applied to heparin sepharose in order to obtain purified haFGF. The purified haFGF was then subjected to automated amino-terminal sequence analysis for 15 cycles. This analysis indicated that all the initiator methionine at position number 1 of FGF155 had been removed during synthesis resulting in the production of an FGF molecule containing 154 amino acids. The amino acids detected in cycles 2–14 of the above analysis were identical to positions 2–14 of FGF155.

Biological activity of the purified haFGF recombinant proteins was demonstrated by the ability to generate new vessels (angiogenesis). The assay involved the study of haFGF influence on the formation of new blood vessels using the model of chicken embryonic chorio-allantoic membrane (CAM).

Several groups have recently established indications for the effective use of angiogenic growth factors to improve blood flow in the presence of tissue ischemia in animal experiments. Yanagisawa-Miwa et al. (1992) Science 257: 1401–1402 demonstrated a significant collateralization together with reduction in the size of the infarct after intracoronary administration of growth factor in rabbits. Baffour et al. (1992) J. Vascul. Surg. 16:181–191 also observed formation of collaterals in ischemic extremities after growth factor administration in animals. Similarly, Albes et al. (1994) Ann. Thorac. Surg. 57:444–449 produced an improvement in the blood flow in ischemic tracheal segments implanted subcutaneously in rabbits by injecting growth factor-enriched fibrin glue locally. Thus, preliminary animal studies suggested that angiogenic factors may be useful in stimulating neoangiogenesis in ischemic tissues.

To date the results of five Phase I human angiogenesis clinical trials using a surgical delivery approach have been published: Stegmann et. al., have published two studies on the protein-based delivery of FGF-1. The first human trial reported by Stegmann involved the injection of FGF-1 while the patients were undergoing a coronary artery bypass procedure (CABG) (Schumacher B, Pecher P, von Specht B U, et al. *Circulation*. (1998) 97:645–650). The second human angiogenesis clinical trial reported by Stegmann was the use of FGF-1 as sole therapy in treating patients with severe coronary artery disease (Stegmann T J, Hoppert T, Schlürmann W, et al. *Cardiac and Vascular Regeneration*. (2000) 1:1–10). Additionally, there is one report on plasmid-mediated delivery of $VEGF_{165}$ (Symes J F, Losordo D W, Vale P R, et al. *Ann.Thorac.Surg*. (1999) 68:830–837). There is one report of adenovirus-mediated delivery of $VEGF_{121}$, (Rosengart T K, Lee L Y, Patel S R, et al. *Circulation*. (1999) 100:468–474). There is one report of protein-based delivery of FGF-2 in a sustained-release heparin alginate formulation (Laham R J, Sellke F W, Edelman E R, et al. *Circulation*. (1999) 100:1865–1871). All these surgical trials followed the strategy of delivery of angiogenic growth factors to myocardial areas of reversible ischemia not amenable to PTCA or CABG. In three of the trials, concomitant CABG was performed—thus making the process of evaluating the results more difficult. In a phase I clinical trial, Symes et al. reported a decrease in angina frequency and severity, and an improvement of myocardial perfusion following intramyocardial injection of plasmid-mediated $VEGF_{165}$, documented by stress SPECT sestamibi imaging.

Also, first clinical experiences were reported regarding non-surgical, catheter-based angiogenic growth factor application. Hendel et al. used intracoronary rhVEGF infusion in different doses in 14 patients (Hendel R C, Henry T D, Rocha-Singh K, et al. *Circulation*. (2000) 101:118–121). They did not find a significant change in stress perfusion scores among the entire group, however, an improvement in global resting perfusion score was noted. Udelson et al. performed in a total of 59 patients intracoronary (n=45) or intravenous (n=14) administration of rFGF-2, resulting in an attenuation of stress induced ischemia (expressed as mean per-segment reversibility score) in all, and improvement in resting myocardial perfusion in 37 patients (Udelson J E, Dilsizian V, Laham R J, et al. *Circulation*. (2000) 102: 1605–1610). With regard to the alternative approach of intrapericardial instillation of growth factors (Laham R J, Simons M, Hung D. Cathet *Cardiovasc Interv*. (1999) 47:109–111; Waxman S, Moreno R, Rowe K A. *J Am Coll Cardiol*. (1999) 33:2073–2077) there remain basic limitations because of imponderable diffusion and resorption of the growth factors, and also because of the high prevalence (80–90%) of prior CABG surgery in this group of patients, excluding the option for such a technique.

According to one preferred embodiment of the present invention, myocardial ischemia resulting from one or more predetermined site(s) of coronary artery stenosis is treated by application of an effective amount of a pharmaceutical composition comprising an angiogenic growth factor and optionally a physiologic "glue" at or near the predetermined site(s) of coronary artery stenosis (see Schmacher et al. (1998) Circulation 97:645–650; the disclosure of which is incorporated herein by reference). While the inventors have found that both acidic fibroblast growth factor (FGF-1) and basic fibroblast growth factor (FGF-2) are effective in promoting neoangiogenesis, the acidic form, designated FGF-1, is presently considered the most effective angiogenic growth factor. Notwithstanding the present preference for human FGF-1, this invention encompasses the broader concept and methods of treating CHD in mammals by providing a site-directed injection within the underperfused myocardium, at or near a vessel stenosis, of a pharmaceutical composition comprising any angiogenic substance optionally with a physiologic glue. Preferably, the angiogenic substance is a recombinant protein.

Accordingly, numerous growth factors have been identified which possess significant angiogenic properties, including: both FGF-1 and FGF-2 (FGF is also known as Heparin Binding Growth Factor (HBGF) and Endothelial Cell Growth Factor (ECGF); see e.g. Schlaudraff et al. (1993) Eur. J. Cardio-thorac. Surg. 7:637–644; Fasol et al. (1994) J. Thorac. Cardiovasc. Surg. 107:1432–1439), which are potent mitogens for both vascular endothelial cells as well as the underlying smooth muscle cells; Vascular Endothelial Growth Factor (VEGF), which is mitogenic for the vascular endothelial cells, but not for the underlying smooth muscle cells (see e.g. Isner et al. (1996) Lancet 348:370–374; Dvorak et al. (1991) J. Exp. Med. 174:1275–1278); angiopoietin-1, which mediates the recruitment of smooth muscle cells to the wall of new vessels (Suri et al. (1996)

Cell 87:1171–1180); angiopoietin-2, which may prevent smooth muscle cell apposition to the walls of microvessels (Maisonpierre et al. (1997) Science 277:55–60); and Platelet Derived Growth Factor (PDGF), Insulin-Like Growth Factors-I and II (IGF-I and IGF-II), and Transforming Growth Factors-α and β, (TGF-α and TGF-β), and Epidermal Growth Factor, (EGF), all of which have been shown to be potent modulators of endothelial and smooth muscle cell growth.

The final dose of angiogenic factor to be applied at or near each vessel stenosis, is preferably in the range of 0.1 µg/kg body weight per site to about 10 mg/kg body weight per site. More preferably, the final dose of angiogenic factor is within the range of about 1 µg/kg body weight per site to about 1 mg/kg body weight per site. Most preferably, the dose of growth factor is in the range of about 10 to 100 µg/kg body weight per site.

A physiologic glue may be optionally included in the pharmaceutical composition in order to enhance the affinity of the growth factor for the ischemic tissue and to prevent the growth factor from rapidly entering the systemic circulation. It is undesirable to have the angiogenic factor enter the systemic circulation for two reasons. First, it would be rapidly diluted to an ineffective concentration, and second, the growth factor may stimulate undesirable growth at sites other than the target site. In one embodiment, FGF-1 is mixed with a physiologic glue, referred to as "fibrin glue", prior to application of the growth factor intramyocardially. In an alternate embodiment, the physiologic glue is added separately from the angiogenic factor.

Fibrin glue typically comprises fibrinogen and thrombin, which react to form a fibrin matrix (see e.g. U.S. Pat. Nos. 4,377,572 and 4,642,120, WO 92/09301, and European Patent No. 0,068,047, which describes an anhydrous powder that is derived from an enriched plasma fraction that contains fibrinogen, a fibrinolysis inhibitor, and thrombin or prothrombin; the disclosures of which are incorporated herein by reference).

Fibrin glue may be purchased from IMMUNO AG or BEHRINGWERKE AG (Germany), as a two-component system comprising a fibrinogen component (trade name, "Tissucoll") and a thrombin component (see U.S. Patent No. owned by IMMUNO AG). The two components are mixed under sterile conditions at 37° C. in a calcium chloride solution in the presence of a protease inhibitor, immediately prior to combining with the angiogenic growth factor and application to the patient. However, while fibrin glue is contemplated in accordance with a preferred mode of practicing the present invention, other "glues" or matrix-forming compositions may also be used in accordance with the present disclosure.

An example of a variation of the fibrin matrix is disclosed in Australian Patent AU-A-75097/87, which describes a biological glue prepared from fibrinogen, factor XIII, a thrombin inhibitor, such as antithrombin III, prothrombin factors, calcium ions, and if necessary, a plasmin inhibitor. Other compounds which have been disclosed as useful in forming biological matrices include: collagen, elastin, Sepharose, gelatin and any other biodegradable material which forms a matrix (see e.g. WO 92/13565 to Hunziker; the disclosure of which is incorporated herein by reference). In some embodiments, it is preferable to administer the angiogenic factor without a matrix-forming composition.

The pharmaceutical composition, comprising the angiogenic growth factor and optionally the physiologic glue is preferably prepared immediately prior to application. The growth factor may be prepared from a sterile concentrated stock solution, rehydrated from a lyophilized powder, or any other stable storage form recognized by those of ordinary skill in the biomedical field, and diluted in a sterile physiologic solution, preferably saline, to give a final volume of about 0.01 to 10 ml, preferably about 1 ml. This solution may optionally contain an anticoagulant, such as heparin, in a final concentration in a range of about 1 U per ml to about 1000 U per ml, or any other anticoagulant known in the art.

The solution containing the angiogenic factor is thoroughly mixed with the freshly prepared glue solution (about 0.01 to 10 ml; preferably about 1 ml) to yield a homogeneous solution containing the desired amounts of growth factor and glue in a volume suitable for injection intramyocardially. The volume of pharmaceutical composition injected per site should be in the range of about 0.02 to 5 ml, preferably not greater than about 2 ml. The pharmaceutical composition should be warmed to about 37° C. prior to application.

In an alternative embodiment, the composition containing angiogenic factor and, optionally, heparin, is injected into the heart wall. The freshly prepared glue solution is subsequently injected to the surface of the heart where the angiogenic factor was injected to prevent leakage or seepage of the angiogenic factor out of the injection site.

The following detailed description of the invention describes a procedure for producing and purifying human fibroblast growth factor-1 (hFGF-1), the preferred angiogenic growth factor in accordance with the present invention. Next, surgical methods for applying the pharmaceutical composition are described. Finally, working examples are presented for preparing, testing and using the pharmaceutical composition of the present invention.

EXAMPLE 1

Production of Human aFGF 154 by Phage-dependent Method

Cultures of *Escherichia coli* BL21(DE3) (NOVAGEN) were transformed by plasmid pET24-155 @rev (FIG. 3), which contains one copy of the chemically synthesized haFGF 155 gene encoding human acidic fibroblast growth factor (155 amino acids) (SEQ ID NO: 1). Cultures of BL21(DE3) contain a single copy of the gene for T7 RNA polymerase under the control of the inducible lac UV5 promoter in the bacterial genome (Studier et al. (1986) J. Mol. Biol. 189:113–130). Into the plasmid pET-24a(+) (NOVAGEN) was inserted the chemically synthesized haFGF 155 gene (SEQ ID NO: 1) under the control of the T7 promoter to produce plasmid pET24-155 @rev. Expression of the haFGF 155 gene begins only after the appearance of T7 polymerase in the cells which is mediated through the induction of the lac UV5 promoter by IPTG.

Cultures of *E. coli* BL21(DE3) with pET24-155 @rev were grown with shaking at 37° C. in LB medium, containing 50 µg/ml kanamycin, to a density of 2×10$^8$ cells/ml. Then the cells were infected with phage λ cI$_{857}$ Q$_{am117}$ R$_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ cI$_{857}$ Q$_{am117}$ R$_{am54}$ was prepared from lysogenic cultures of *E. coli* RLMI, which were grown in LB medium at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1$–$2\times10^{10}$ PFU/ml.

After incubation with the phage-infected cells for 14 hours, debris was removed from the culture medium by centrifugation. The culture medium, containing the haFGF 154 protein was applied to a heparin sepharose column to obtain pure haFGF 154.

Figure 4:
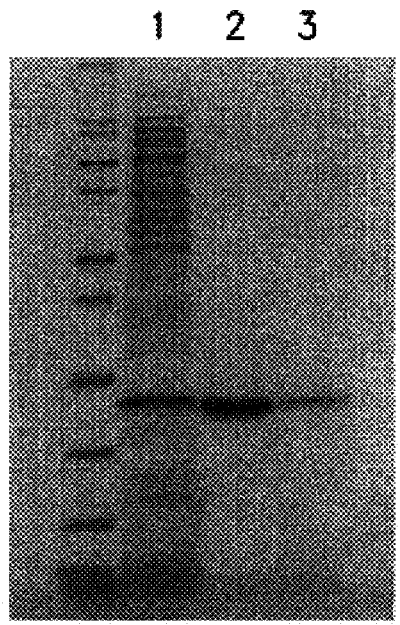
FIG. 4 shows purification of the culture medium containing recombinant haFGF 154 (SEQ ID NO: 8). In the electrophoregram: lane 1, crude media containing recombinant haFGF 154 (225 mg FGF-1/liter); lane 2, Heparin-Sepharose column purified recombinant haFGF 154; lane 3, purification of haFGF 154 by HPLC C-18 column. The unlabelled lane at the far left contains molecular weight markers.

The culture medium containing the haFGF 154 was analyzed by SDS-polyacrylamide gel electrophoresis under denaturing conditions and stained with Coomassie Blue. An electrophoregram of the culture medium, containing haFGF 154 protein is compared to purified haFGF protein in FIG. 4. Lane 1 shows crude media containing recombinant haFGF 154 (225 mg FGF-1/liter). Lane 2 shows Heparin-Sepharose column purified recombinant haFGF 154. Lane 3 shows purification of haFGF 154 by HPLC C-18 column. The unlabelled lane at the far left contains molecular weight markers. The overall purification yield was about 65%. Bioactivity was measured by two different assays, a 3T3 cell proliferation assay and a rat hind limb angiogenesis assay (not shown). The bioactivity was equipotent with FGF-1 obtained from Sigma-Chem. An assay using chicken embryo chorio-allantoic membrane is shown in Example 7, below.

The production of haFGF 154 protein in phage-infected cultures was about 20% of the total cellular protein. The molecular weight of haFGF 154 was 17,908 Daltons as determined by densitometer Image Master VDS (data not shown). N-terminal sequence analysis of FGF 154 indicated an-alanine residue at the first position, with no initiator methionine detected.

EXAMPLE 2

Production of Human aFGF 134 Amino Acid form by Phage-dependent Method

Figure 5:
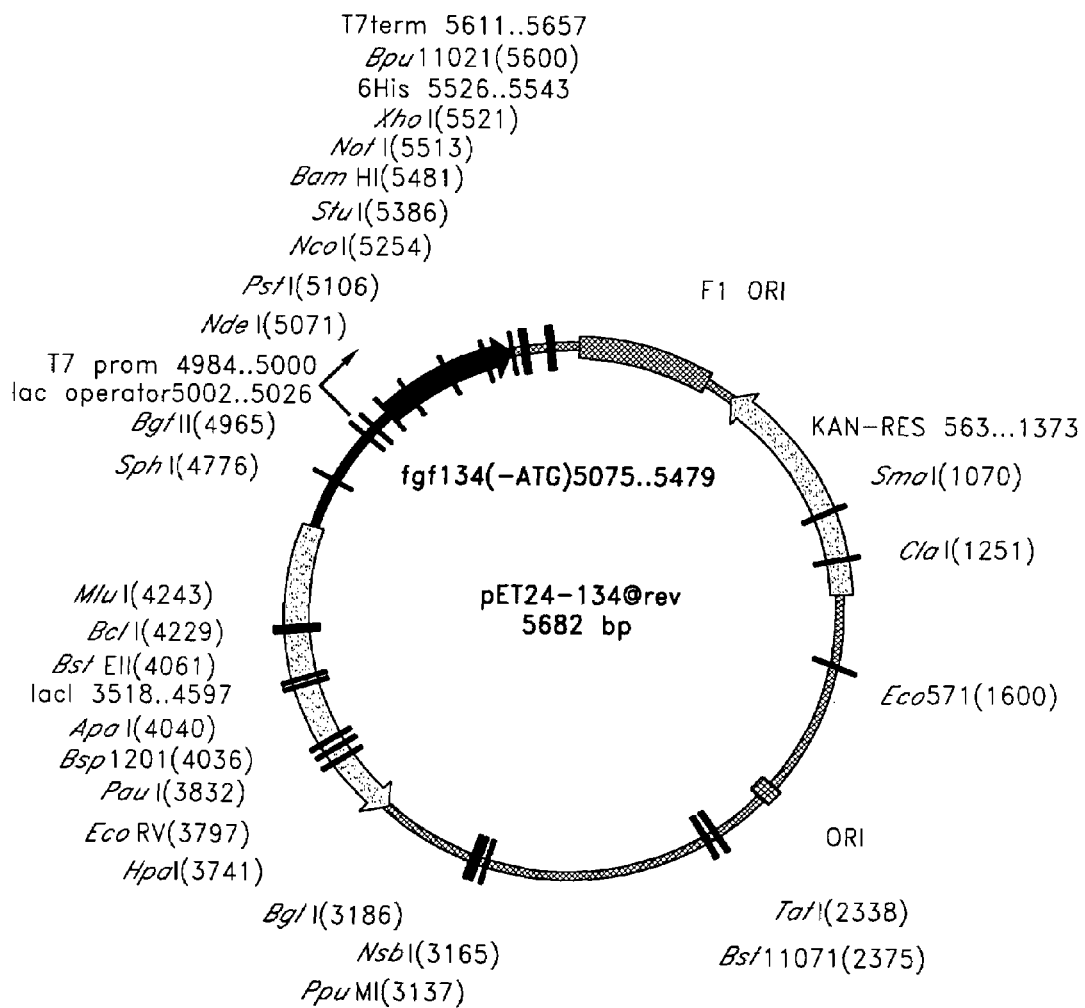
FIG. 5 shows the pET24-134@rev construct which contains the chemically synthesized haFGF 134 gene (SEQ ID NO: 4).

Cultures of *Escherichia coli* BL21(DE3) (NOVAGEN) were transformed by plasmid pET24-134 @rev (FIG. 5), which contains one copy of the chemically synthesized gene encoding human aFGF 134 amino acid form (FIG. 6; SEQ ID NO: 4). The translated amino acid sequence is shown in SEQ ID NO: 5. Cultures of BL21(DE3) contain a single copy of the gene for T7 RNA polymerase under the control of the inducible lac UV5 promoter in the bacterial genome (Studier et al. (1986) J. Mol. Biol. 189:113–130). Into the plasmid pET-24a(+) (NOVAGEN) was inserted the human aFGF 134 amino acid form gene under the control of the T7 promoter. Expression of the human aFGF 134 amino acid form gene begins only after the appearance of T7 polymerase in the cells which is mediated through the induction of the lac UV5 promoter by IPTG.

Cultures of *E. coli* BL21(DE3) with pET24-134 @rev were grown with shaking at 37° C. in LB medium, containing 50 μg/ml kanamycin, to a density of $2\times10^8$ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Qam_{117}$ $R_{am54}$ was prepared from lysogenic cultures of *E. coli* RLMI, which were grown in LB medium at 30° C. with intensive aeration to a density of approximately $1\times10^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1$–$2\times10^{10}$ PFU/ml.

After incubation with the phage-infected cells for 14 hours, debris was removed from the culture medium by centrifugation. The culture medium containing the haFGF 134 amino acid form was applied to a heparin sepharose column to obtain pure human aFGF 134 amino acid form.

EXAMPLE 3

Production of Human aFGF 140 Amino Acid form by Phage-dependent Method

Figure 7:
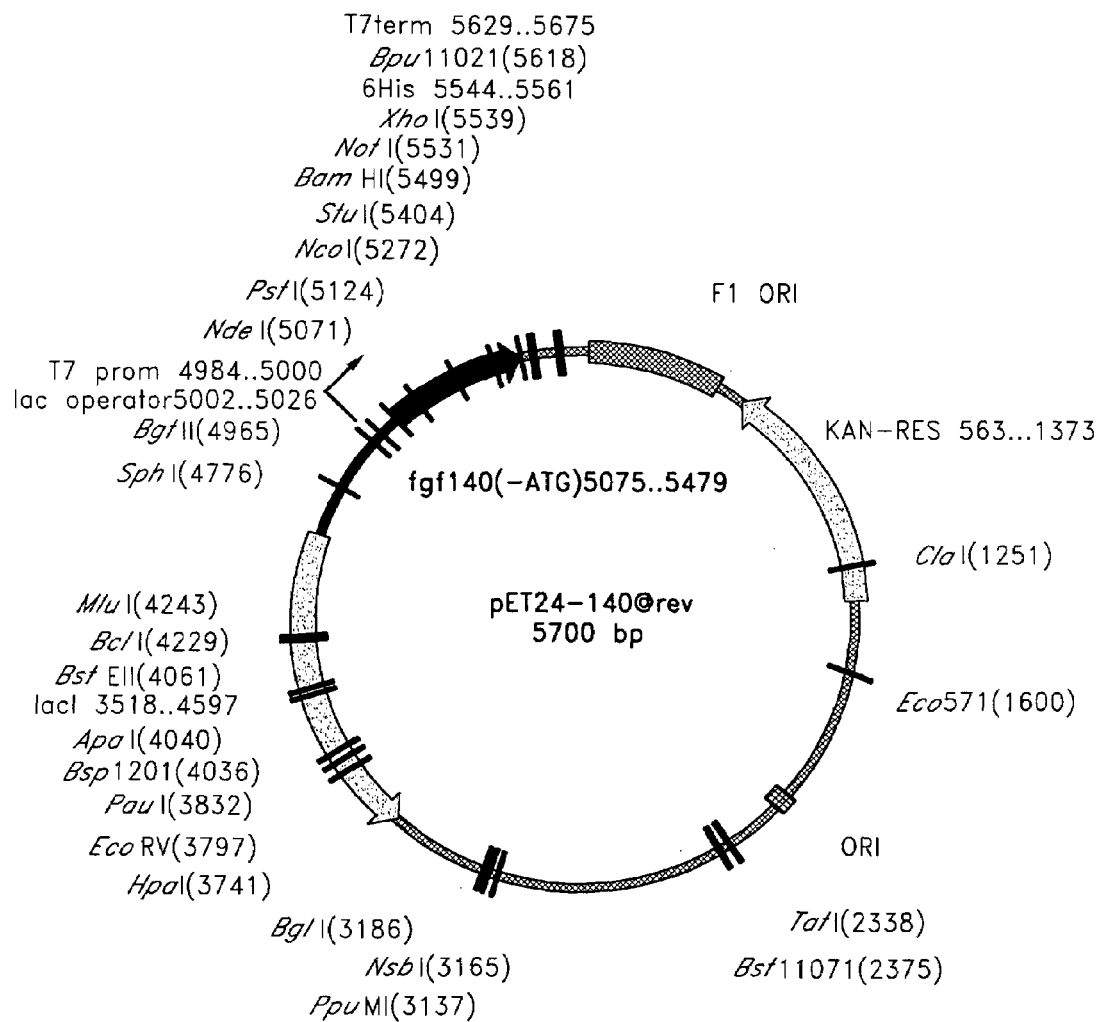
FIG. 7 shows the pET24-140@rev construct which contains the chemically synthesized haFGF 140 gene (SEQ ID NO: 6).

Cultures of *Escherichia coli* BL21(DE3) (NOVAGEN) were transformed by plasmid pET24-140 @rev (FIG. 7), which contains one copy of the chemically synthesized gene encoding human aFGF 140 amino acid form (FIG. 8; SEQ ID NO: 6). The corresponding protein is shown as SEQ ID NO: 7. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 140 amino acid form gene under the control of the T7 promoter. Expression of the human aFGF 140 amino acid form gene begins only after the appearance of T7 polymerase in the cells which is mediated through the induction of the lac UV5 promoter by IPTG.

Cultures of *E. coli* BL21(DE3) with pET24-140 @rev were grown with shaking at 37° C. in LB medium, containing 50 μg/ml kanamycin, to a density of $2\times10^8$ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Qam_{117}$ $R_{am54}$ was prepared from lysogenic cultures of *E. coli* RLMI, which were grown in LB medium at 30° C. with intensive aeration to a density of approximately $1\times10^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1$–$2\times10^{10}$ PFU/ml.

After incubation with the phage-infected cells for 14 hours, debris was removed from the culture medium by centrifugation. The culture medium containing the haFGF 140 amino acid form was applied to a heparin sepharose column to obtain pure human aFGF 140 amino acid form.

Human aFGF 140 produced by the method disclosed above had biological activity based upon the chick membrane assay (Example 6).

EXAMPLE 4

Production of Human aFGF 146 Amino Acid form by Phage-dependent Method

Cultures of *Escherichia coli* BL21(DE3) (NOVAGEN) were transformed by plasmid pET24-146 @rev, which contains one copy of the chemically synthesized gene encoding human aFGF 146 amino acid form. Cultures of BL21 (DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 146 amino acid form gene under the control of the T7 promoter. Expression of the human aFGF 146 amino acid form gene begins only after the appearance of T7 polymerase in the cells which is mediated through the induction of the lac UV5 promoter by IPTG.

Cultures of *E. coli* BL21(DE3) with pET24-146 @rev were grown with shaking at 37° C. in LB medium, containing 50 µg/ml kanamycin, to a density of 2×10⁸ cells/ml. Then the cells were infected with phage λ $cI_{857}$ $Q_{am171}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately 1×10⁸ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10¹⁰ PFU/ml.

After incubation with the phage-infected cells for 14 hours, debris was removed from the culture medium by centrifugation. The culture medium, containing the haFGF 146 amino acid protein, was applied to a heparin sepharose column to obtain pure human aFGF 146 amino acid form.

Human aFGF 146 produced by the method disclosed above had biological activity based upon the chick membrane assay (Example 6).

EXAMPLE 5

Purification of haFGF

The culture medium containing haFGF is diluted with one volume of 0.04M $KH_2PO_4$ buffer, pH 7.0, and applied to a heparin-sepharose column equilibrated with 0.02 M $KH_2PO_4$, pH 7.0. The flow rate is adjusted to 80 ml/hour. After application of the culture medium containing the haFGF protein, the column is washed with 0.02M $KH_2PO_4$ buffer, pH 7.0. Next, the column is washed with 0.02 M $KH_2PO_4$ buffer containing 0.6M NaCl, pH 7.3. Elution is carried out using 0.02 M $KH_2PO_4$ buffer with 1.5 M NaCl, pH 7.5. All steps are carried out at 4° C.

EXAMPLE 6

Gel Analysis of Recombinant Proteins Produced by the Phage-dependent Method.

Figure 9:
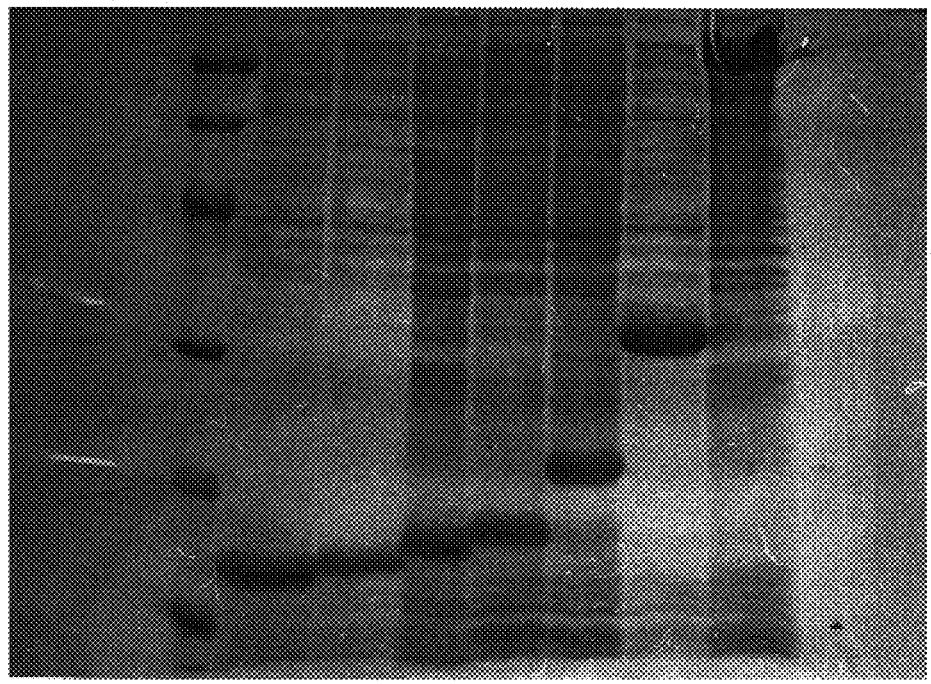
FIG. 9 shows a 12.5% SDS polyacrylamide gel containing proteins produced by the phage-dependent method described herein: lane 1: molecular weight standards, 2 μg each standard; lane 2: 40 μl of culture media containing the recombinant FGF 134 protein; lane 3: 40 μl of culture media containing the recombinant FGF 140 protein; lane 4: 40 μl of culture media containing recombinant interferon a2B; lane 5: 40 μl of culture media containing recombinant FGF 154 protein; lane 6: 40 μl of culture media containing recombinant human growth hormone; lane 7: 40 μl of culture media containing recombinant methionine aminopeptidase; lane 8: 40 μl of culture media containing β-galactosidase of E. coli.

Culture media containing human aFGF 134 amino acid form, human aFGF 140 amino acid form, and human aFGF 154 amino acid form were analyzed by SDS-polyacrylamide gel electrophoresis under denaturing conditions and stained with Coomassie Blue. An electrophoregram of culture media, containing human aFGF 134 amino acid form, human aFGF 140 amino acid form, human and aFGF 146 amino acid form was compared to molecular weight standards in FIG. 9. Lane 2 shows 30 µl of the culture medium containing human aFGF 134 amino acid form. Lane 3 shows 30 µl of culture media containing the recombinant FGF 140 protein. Lane 5 shows 30 µl of culture media containing recombinant FGF 154 protein. Lane 1 shows 2 µg of each molecular weight standard (Amersham Pharmacia Biotech). From the top, the molecular weight standards are: 94,000; 67,000; 43,000; 30,000; 20,100; and 14,400.

Quantitation of amounts of human aFGF 134 amino acid form, human aFGF 140 amino acid form, and human aFGF 154 amino acid form, in a mixture was accomplished by scanning the stained protein bands on a polyacrylamide gel with densitometer Image Master VDS (Pharmacia Biotech). The production of the recombinant proteins in phage-infected cultures was about 20% of the total cellular protein.

Figure 10:
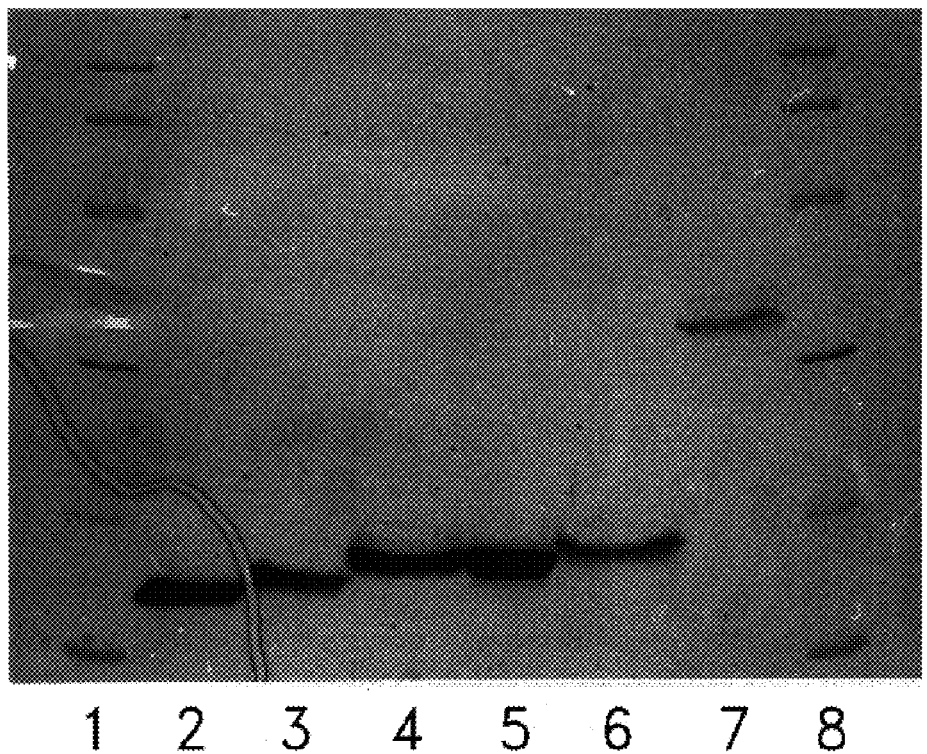
FIG. 10 shows a 12.5% SDS polyacrylamide gel containing recombinant proteins purified according to the presently claimed invention: lane 1: molecular weight standards; lane 2: 5 μg of purified FGF 134 protein; lane 3: 5 μg of purified FGF 140 protein; lane 4: 5 μg of purified FGF 146 protein; lane 5: 5 μg of purified interferon α2B protein; lane 6: 5 μg of purified FGF 154 protein; lane 7: 5 μg of purified methionine amino peptidase protein; and lane 8: molecular weight standards.

An electrophoregram containing purified recombinant human aFGF 134, haFGF 140, haFGF 146, and haFGF 154 protein was compared to molecular weight standards (FIG. 10). Lane 2 shows 5 µg of the purified aFGF 134 protein. Lane 3 shows 5 µg of the purified human aFGF 140. Lane 4 shows 5 µg of the purified human aFGF 146 amino acid form. The production of human aFGF 146 amino acid form in phage-infected cultures was about 20% of the total cellular protein. Lane 6 shows 5 µg of haFGF 154 protein. Lanes I and 8 show 2 µg of each molecular weight standard (Amersham Pharmacia Biotech).

EXAMPLE 7

A Method of Studying FGF Influence on the Formation of New Blood Vessels in the Chicken Embrvo Chorio-allantoic Membrane (CAM).

The method of studying angiogenesis on the model of chicken embryos (Thomas et al. (1985) Proc. Natl. Acad. Sci, USA 82:6409–6413) was adapted to determine the effects of the haFGF 154, 146, and 140 recombinant proteins on angiogenesis compared to pure brain-derived acidic fibroblast growth factor. Pure brain-derived acidic fibroblast growth factor is a potent angiogenic vascular endothelial cell mitogen with sequence homology to interleukin.

The shells of three-day old chicken embryos were sterilized with ethyl alcohol. The shell and under shell cover were removed from the air chamber using forceps and the eggs were covered by the bottom of a plastic 35 mm Petri dish. The embryos were incubated at 37° C. for 5–6 days. At the end of this period, the embryos were examined and the eggs with well-developed blood vessels of CAM were selected for experimentation.

Filter paper disks with deposited gel containing FGF were laid on the eggs CAM with the gel towards the blood vessels and incubated in a thermostat at 37° C. for another 3 days. The gel was prepared in the following way: the tested quantity of FGF was dissolved in 30 µl of Eagle's medium (solution 1); then in 30 µl of Eagle's medium, 10 µg of heparin was dissolved and 2% of agarose added (solution 2). Then equal volumes of solution 1 and 2 were mixed and the obtained mixture was deposited in aliquots by 60 µl on 12 mm diameter filter paper disks.

On the 4$^{th}$ day, the filter paper disks were removed. Rich cow milk (10% milkfat) was injected under CAM in a quantity of about 1 ml or less. The result was a white background against which the CAM vessels were easily observed.

The results of the experiment were recorded with a video camera in conjunction with a computer. The formation of new CAM vessel under the affect of FGF was evaluated by the following parameters: the nature and direction of vessel growth, their quantity and quality (large, medium, small), the presence or absence of anastomosis, etc. These data were compared with the control samples which had not been exposed to FGF. FIG. 11 shows Chicken embryo blood vessels on the 14$^{th}$ day of development after treatment with FGF154 produced by the phage-dependent recombinant method described herein and purified on heparin sepharose as described.

Figure 11A:
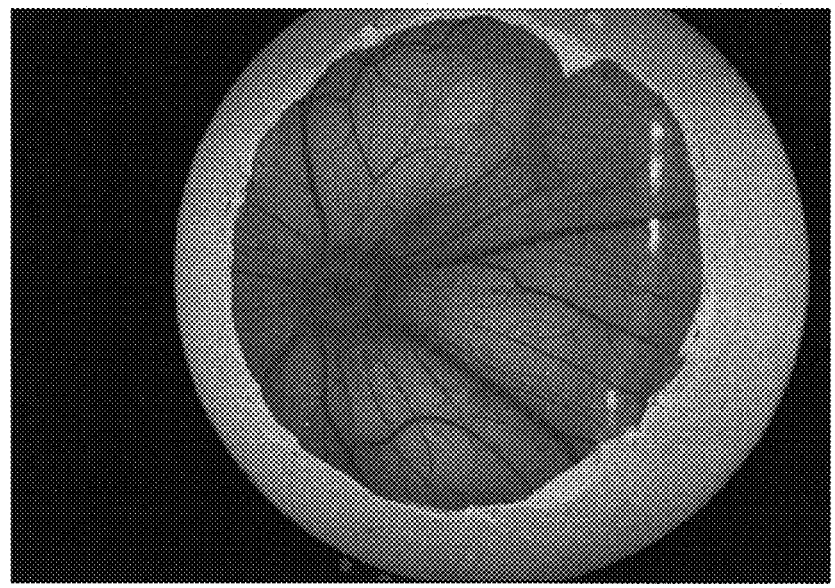
FIG. 11A shows the effect of 1 μgm of the 154 amino acid form of the haFGF protein. The vessels under application are mainly small and show radial growth.
Figure 11B:
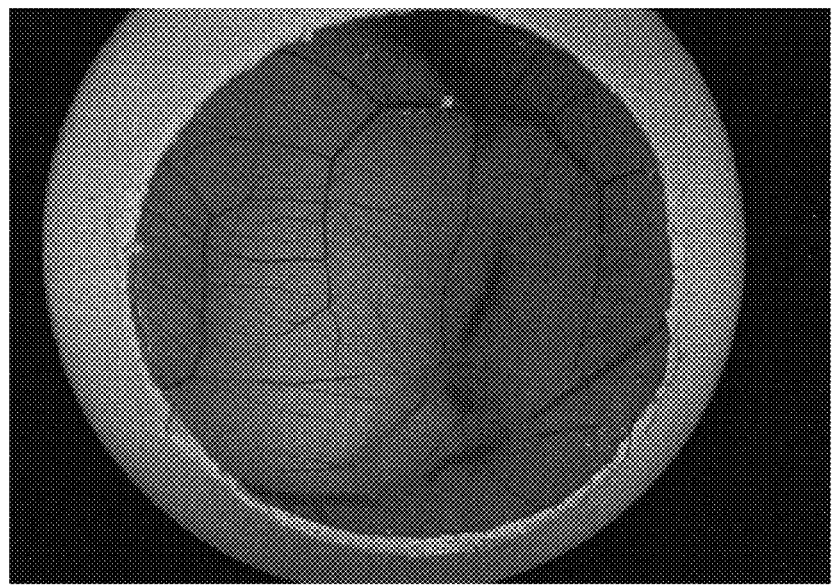
FIG. 11B shows the control sample.

FIG. 11A demonstrates the correlation between application of recombinant FGF154 protein and the formation of new blood vessels. On the fourth day after application of 1 µg of FGF154, vessels are mainly small and show radial growth (FIG. 11A). Increasing the amount of FGF 154 to 3 µg results in a corresponding increase in the size of the blood vessels (not shown). Medium vessels are observed with radial growth. A further increase to 4 μg of FGF154 applied (not shown) results in development of large, medium and small blood vessels at 4 days after application. Untreated control is shown in FIG. 11B.

EXAMPLE 8

Application of the Pharmaceutical Composition: Surgical Methods

The patient was placed in a supine position on the operating table and prepared and draped for a standard anterior left-sided thoracotomy incision. The left hemithorax was slightly elevated. Routine general anesthesia was induced via endotracheal intubation; the routine monitoring for open heart procedures including central venous and arterial lines was established. A left-sided curved transverse skin incision of six to eight centimeters was performed over the 5th rib anteriorly. Following minimal muscle dissection, the costal cartilage was divided at its junction with the end of the rib, and the left pleural space was entered. The pericardium was opened, and traction sutures were placed to retract the heart forward and to obtain stability of the operative field. The traction sutures also prevented the insufflated left lung from obscuring the surgeon's view.

The coronary artery system and its branches were explored and the lesions to be treated were identified. The described technique allowed access to the anterior (LAD), lateral (Cx) and apical portions of the heart, and the inferior diaphragmatic surface (RCA) as well if necessary. A β-blocker, such as Esmolol, was administered intravenously by the anesthesiologist, and the heart rate was reduced to about 20–60 beats per minute, preferably about 40–60 beats per minute.

The angiogenic pharmaceutical composition was prepared as detailed above, immediately prior to application. A suitable volume containing the desired dose of angiogenic growth factor was taken up in a syringe and administered intramyocardially using a standard 20 gauge needle into the target region of the underperfused myocardium. A maximum of three injections were generally performed, one each for the LAD, Cx, and RCA vascular beds. Each injection had to be performed in strong connection to the course of the native stenosed coronary artery. After completing the injection(s) and ascertaining that there was no bleeding, the pericardium was left open, a chest tube was inserted into the left pleural space, and the surgical incision was closed in the usual manner without pericostal sutures. The skin incision was closed using running reabsorbable suture material. The chest tube was required for about 12 to 24 hours. The patient was extubated in the operating room and postoperatively monitored in the usual manner for 24 hours. The average hospitalization was three days.

It is anticipated that catheter-based techniques may also be used for delivery of the angiogenic composition to the sites of stenosis. Indeed, catheters having steering means and application actuators are presently being used for ablation procedures in the atrial chambers and the delivery of local-acting pharmaceuticals and radiation doses at or near sites of vessel stenosis. Thus, percutaneous intraluminal catheter-based delivery means are also encompassed within the present disclosure.

EXAMPLE 9

Examples of Preparing, Testing and Using the Pharmaceutical Composition Preparation of Fibrin Glue In order to enhance the affinity of the growth factor for the myocardium, the growth factor was mixed with a physiologic glue referred to as "fibrin glue" prior to introduction in situ. A two-component human fibrin glue system was purchased from IMMUNO AG, Heidelberg, Germany). The fibrin glue was prepared using a "Fibrinotherm" temperature-controlled apparatus under sterile conditions.

First the apparatus was set to an operating temperature of 37° C. At the same time, the fibrinogen component ("Tissucoll") was slowly thawed to room temperature. Then 19.6–26.5 mg of bovine thrombin-S and 3 ml of an aprotinin calcium chloride solution (with 3000 units kallidinogenase inactivator and 5.88 mg calcium chloride) were heated to a temperature of 37° C. The thrombin-S was combined with the aprotinin calcium chloride solution by pipetting under sterile conditions, mixed for 10 min with the magnetic stirrer and let stand at 37° C. The thawed "Tissucoll" material was dissolved in the calcium chloride solution, thoroughly mixed, and returned to the heating apparatus. Before use, all the solutions were completely homogeneous. In addition, care was taken that the solutions were stored at 37° C. until the time they were used.

Mixture of Growth Factor and Fibrin Glue

Recombinant hFGF-1 (40 μg) was dissolved in 360 μl PBS-CMF (dilution 1:10), mixed, divided into 40×10 μl aliquots, and stored at −20° C. The quantity of growth factor used for one implantation was 10 μg (or 0.01 mg) per kg body weight of the diluted pure substance for each application site. Addition of the growth factor to the fibrin glue was carried out immediately prior to application, in the operating room. Since 1 ml of thrombin-S and 1 ml of "Tissucoll" were needed for each fibrin glue application, a 2 ml glue amount per implantation was used. After the stock solution of thrombin-S was prepared and ready at 37° C. in the "Fibrinotherm," 1 ml was removed, mixed in a sterile tube with 10 μl of hFGF-1 and the combined quantity was then taken up into the application syringe. At the same time, 1 ml of "Tissucoll" stock solution was taken up into a second sterile syringe. Both the syringes containing the thrombin-S and the "Tissucoll" were stored at 37° C. until combined and administered to the patient.

EXAMPLE 10

In Vitro Studies

In in vitro experiments, we demonstrated the proliferative and mitogenic effects of the growth factor on human saphenous vein endothelial cells. Endothelial cell cultures with added growth factor induced a confluent monolayer after only 5 to 9 days, whereas the monolayer was not complete before 7 to 11 days in the control group (data not shown). In addition, to determining the total cell count with a cell counter, we also confirmed this result by analyzing the rate of DNA synthesis by measuring the incorporation of $^3$H-thymidine into the endothelial cell nuclei using the methods of Klagsbrun and Shing. The cell proliferative potency of hFGF-1 could be further intensified by adding heparin, a glycosaminoglycan protecting the growth factor from inactivation by cellular enzymes and from inactivation by cellular enzymes and from heat and chemical denaturation.

Exclusion of the Progenicity of hFGF-1

Varying concentrations of recombinant hFGF-1 (0.01, 0.5, or 1.0 mg/kg body weight) were injected subcutaneously, intramuscularly, or intravenously into 27 New Zealand White rabbits, the solvent alone being used for an additional 13 controls. Thereafter, the rectal temperature was taken every half hour for 3 hours, hourly for the rest of the day, and every 8 hours for 12 days. A daily white cell count was also repeated for 12 days. In addition to this, the erythrocyte sedimentation rate and the C-reactive protein values were determined on the 3rd, 6th, 9th, and 12th days after the injection.

Pyrogenic effects of the human growth factor produced in this way were definitively ruled out in the animal model. There was no significant rise of body temperature when checked at short intervals and no trace of an inflammatory reaction in comparison with the control group (n=13) in any of the 27 test animals during the period of observation. This result was independent of the concentration and the route of administration (intravenous, subcutaneous, or intramuscular) of the factor.

Exclusion of Tumor Stimulation by hFGF-1

To rule out the oncoproliferative effect of the growth factor, we did stimulation tests on human tumor cell lines. We investigated the following tumors by means of $^3$H-thymidine assays: pleomorphocellular sarcoma, hypernephroma, melanoma and small-cell lung cancer. The initial number of cells was 500 cells per well in 96-well plates. The tumor cell cultures were stimulated with different factor concentrations (10 and 100 ng hFGF-1). The total duration of stimulation was 24 hours.

In addition, human tumor cell lines were implanted in animal experiments for further preclusion of tumorigenicity. An initial dose of $3\times10^6$ cells were implanted subcutaneously in a total of 80 nude mice. For this purpose, the tumor cells were taken up in 0.1 ml culture medium and injected subcutaneously into the right abdomen in the nude mice. The test animals were divided into four groups per tumor cell line: group 1 (n=20) received only tumor cells, group 2 (n=20) received tumor cells and systemic hFGF-1, group 3 (n=20) received a suspension of the tumor cells and growth factor, and group 4 (n=20) received only growth factor. Blood was taken from the animals and their live weight determined at 4-day intervals. After a test duration of 12 weeks, the tumors were explanted, their size and weight determined, and they were afterwards worked up histologically.

In the stimulation test carried out on various human tumor cell lines, possible tumor-stimulating effects of hFGF-1 were ruled out. An increased rate of DNA synthesis compared to the respective controls was not seen in any of the tumor cell lines. Moreover, hFGF-1 also failed to increase tumor cell growth in nude mice. Likewise, neither histological changes in tumors nor changes in the levels of tumor specific polypeptides were seen in animals treated with the growth factor. It is postulated that FGF receptor down-regulation following exposure to hFGF-1 resulted in a decreased ability of the growth factor to stimulate tumor cell growth. Thus, HFGF-1 treatment was not associated with any tumorigenic activity.

EXAMPLE 11

Angiogenic Potency of HFGF-1 in Animal Experiments

Supplementary to our earlier experiments, the effect of hFGF-1 was also investigated in the ischemic hearts of inbred Lewis rats (a total of 275 animals, including 125 controls treated with heat-denatured hFGF-1, 70° C. for 3 minutes). The pericardium was opened via the abdominal wall and diaphragm, and two titanium clips were inserted at the apex of the left ventricle to induce myocardial ischemia. Growth factor (mean concentration of 10:g) was then injected locally into the site. The coronary vessel system was imaged by aortic root angiography after 12 weeks and, finally, a specimen from the same myocardial region was evaluated histologically.

Figure 12A:
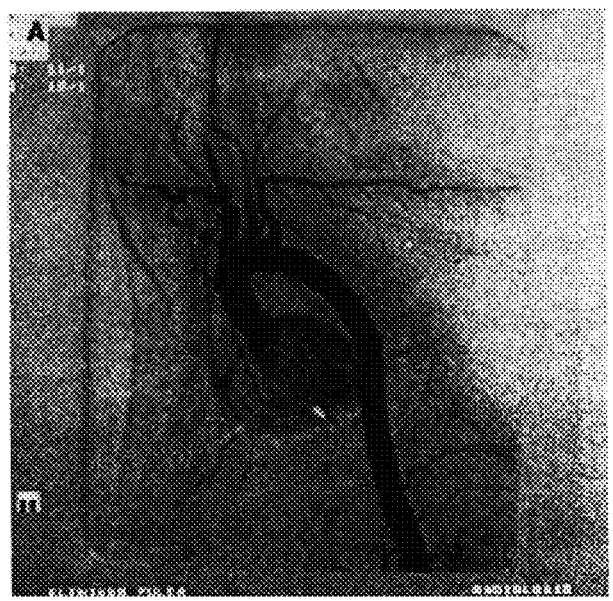
FIG. 12(A) is an angiograph showing clearly discernible accumulation of contrast medium at the site of injection in ischemic rat heart. (B) shows no discernible accumulation of contrast medium in the control group. HBGF-I denotes hFGF-1.
Figure 12B:
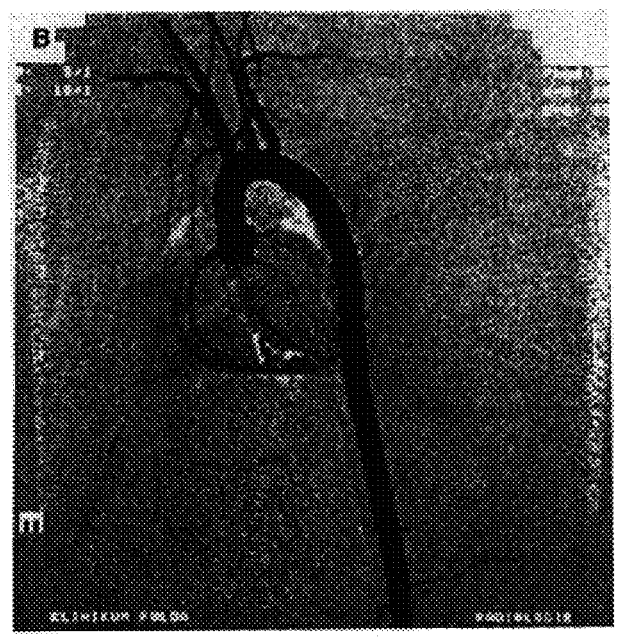

Proof of induced neoangiogenesis was found in the ischemic rat heart. In the test animals, in which myocardial ischemia had previously been induced with titanium clips and growth factor had subsequently been injected into the myocardium, a manifest accumulation of contrast medium was shown by aortic angiography at the site of the hFGF-1 injection 12 weeks later (FIG. 12A), whereas such an accumulation of contrast medium did not appear in any of the control animals (FIG. 12B). Histological examination of the myocardium revealed a threefold increase in the capillary density per square millimeter around the site of the hFGF-1 injection. HBGF-I denotes hFGF-1.

EXAMPLE 12

Clinical Use of Recombinant hFGF-1 in Combination with Coronary Artery Bypass Graft in Patients with CHD This study was approved by the Medical Research Commission at the Phillips University of Marburg on Aug. 10, 1993 (No. 47.93). Twenty patients without any history of infarction or cardiac surgery (14 men and 6 women; minimum age, 50 years) were subjected to an elective bypass operation for multivessel coronary heart disease. The growth factor was applied directly during the operation. As a control group, 20 patients who underwent the same procedure were given heat-denatured recombinant hFGF-1 (70° C. for 3 minutes). The choice of treatment was completely random, the names being placed in sealed envelopes and selected in a blinded manner.

The details, nature, and aims of this procedure were explained beforehand to every patient who underwent the operation. In all cases, their fully informed consent was received. Both groups of patients were closely comparable with regard to clinical symptoms, accompanying disorders, cardiovascular risk factors, ventricular function, sex, and age. A comparable coronary morphology was found in both groups.

All patients had a further stenosis in the distal third of the LAD or at the origin of one of its branches in addition to a severe proximal stenosis. The mean ejection fraction of the left ventricle for all patients was 50%. The operative procedure for coronary revascularization with autologous grafts (an average per patient of 2 to 3 venous bypasses and 1 from the left IMA) was routinely performed. Recombinant hFGF-1 (mean concentration, 0.01 mg/kg body weight) was injected into the myocardium distal to the IMA/LAD anastomosis and close to the LAD, during the maintenance of the extracorporeal circulation and after completion of the distal anastomosis. In the control group, heat-denatured recombinant hFGF-1 was substituted for active recombinant hFGF-1. After 12 weeks, the IMA bypasses of all the patients were imaged selectively by transfemoral, intra-arterial, and digital subtraction angiography.

Angiograms obtained in this way were evaluated by means of EDP-assisted digital gray-value analysis, a universally recognized and well-established technique for demonstrating capillary neoangiogenesis. Sites of interest both with and without recombinant hFGF-1 (meaning heat-denatured recombinant hFGF-1) were selected in the vessels filled with contrast medium and in regions of the myocardium distal to the IMA/LAD anastomosis. One hundred pixels were selected from each site of interest and analyzed digitally. Complete blackening of the x-ray films was rated with a gray value of 150, and areas without blackening of the film were allotted a zero value. During the first 5 postoperative days, separate laboratory checks in addition to the routine postoperative follow-up procedures were made twice daily, and the temperature checked three times a day.

Figure 13A:
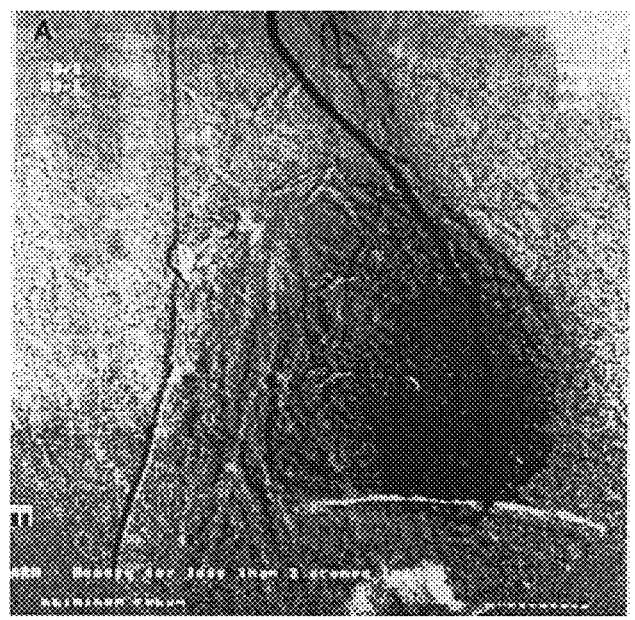
FIG. 13(A) is an angiograph showing a pronounced accumulation of contrast medium compared with the control group after injection of the growth factor into the human heart. (B) shows no increase in the accumulation of contrast medium around the IMA/LAD anastomosis. HBGF-I indicates hFGF-1.
Figure 13B:
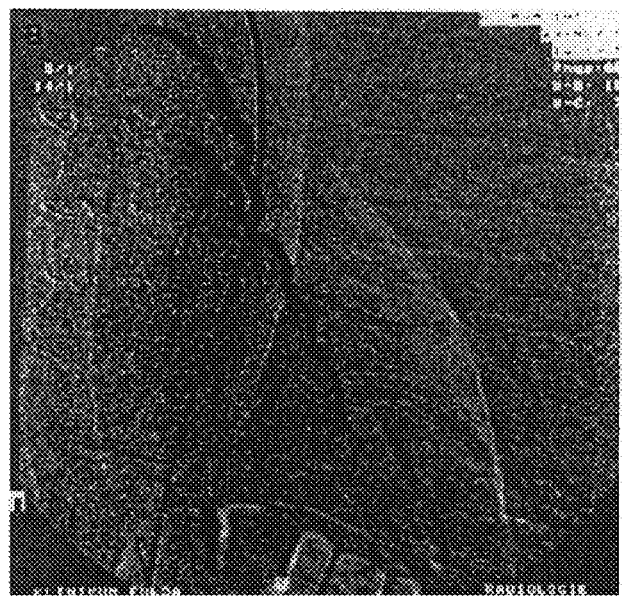

When the growth factor recombinant HFGF-1 was used clinically for the first time on the human heart, neoangiogenesis together with the development of a normal vascular appearance could be demonstrated angiographically. Selective imaging of the IMA bypasses by intra-arterial digital subtraction angiography confirmed the following result in all 20 patients: at the site of injection and in the distal areas supplied by the LAD, a pronounced accumulation of contrast medium extended peripherally around the artery for ≈3 to 4 cm, distal to the IMA/LAD anastomosis (FIG. 13A). HBGF-I denotes recombinant hFGF-1. In the control angiograms of patients to whom only heat-denatured recombinant hFGF-1 had been given, the IMA/LAD anastomosis was also recognizable, but the accumulation of contrast medium described above was absent (FIG. 13B). The angiograms of both the treated and control groups were recorded at a rate of four images per second, and these show comparable distances between the beginning of the injection and visualization of the medium.

Figure 14A:
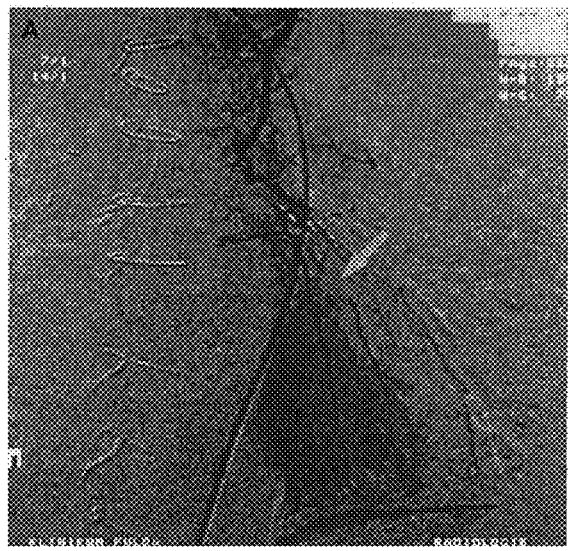
FIG. 14(A) is an angiograph showing collateralization of stenoses (arrow): a diagonal branch occluded just distal to its origin was filled through the newly grown capillaries. (B) shows collateralization of stenoses (arrow) by newly grown capillaries: the peripherally stenosed LAD was filled through these vessels. HBGF-I indicates hFGF-1.
Figure 14B:
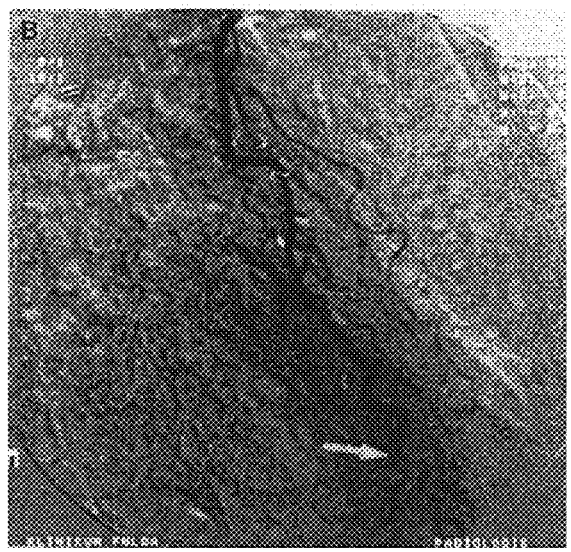

At the site of injection of the recombinant hFGF-1, a capillary network could be seen sprouting out from the coronary artery into the myocardium. This enabled retrograde imaging of a stenosed diagonal branch to be performed (FIG. 14A). such "neocapillary vessels" can also provide a collateral circulation around additional distal stenoses of the LAD (FIG. 14B) and bring about retrograde filling of a short segment of the artery distal to the stenosis. In none of the angiograms of the treated patients taken 12 weeks after the operation were any new stenoses of the LAD detectable.

Figure 15:
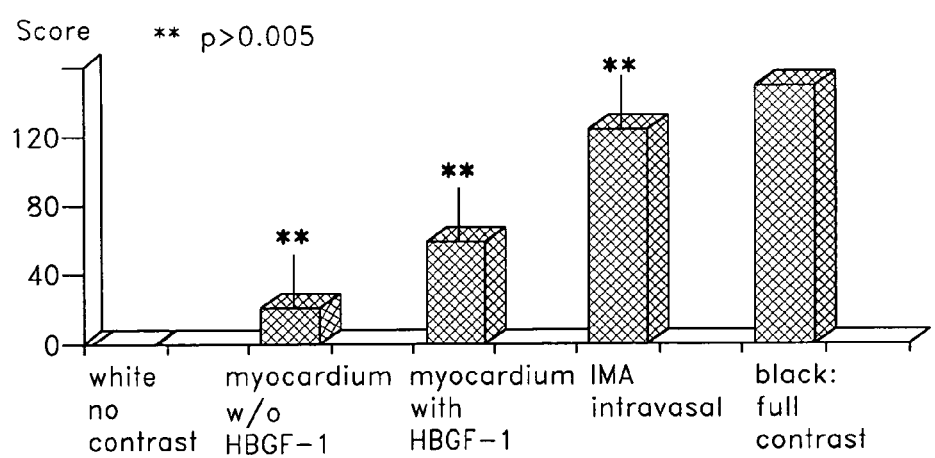
FIG. 15 is a quantitative gray value analysis of contrast medium accumulation in the angiography showing a two-threefold increase in local blood flow at the site of injection. HBGF-I indicates hFGF-1.

The results of EDP-assisted digital gray value analysis for quantification of the neoangiogenesis (FIG. 15) gave a mean gray value of 124 for the vessels. The control myocardium reached a gray value of only 20, and that of the myocardium injected with recombinant hFGF-1 gave a value of 59 (FIG. 15).

Importantly, the angiographic evidence of neovascularization was supported by enhanced ejection fractions in patients receiving recombinant hFGF-1, three years after surgery. The improvement in the blood supply, suggested post-operatively by angiography, was confirmed by results showing enhanced ejection fraction. Suprisingly, the improved vacularization as evidenced by enhanced ejection fraction was evident by echocardiographic follow up three years after the procedure. Indeed, the general ejection fraction in the study group improved from 50.3% before the operation to 63.8% after three years, whereas the the control group increased from 51.5% to only 59.4% within the same time period. These ejection fraction data were not predicted by the earlier animal studies and provide the first demonstration that neoangiogenesis in human myocardium is associated with an enhanced index of clinical function. Similarly, patients improved from NYHA III classification before the operation to NYHA I-II three years post-op. The marked improvement in cardiac function three years after growth factor therapy was suprising in view of the frequent incidence of restenosis in such patients.

On the basis of these in vitro and in vivo experiments, the efficacy of recombinant hFGF-1 for inducing neoangiogenesis in situ in the ischemic human heart and for treating CHD were established for the first time.

EXAMPLE 13

Clinical Use of Recombinant HFGF-1 (140) as Sole Therapy in Patients with CHD

In this Example, hFGF-1 therapy is used as the sole treatment, that is, a coronary artery bypass graft was not performed in addition to the FGF-1 treatment as in Example 12. The patient population included in this trial exactly met the general accepted criteria for angiogenic therapy: small vessel disease and/or additional involvement of peripheral coronary artery branches into the atherosclerotic disease. During the study, two main aspects of FGF-1 therapy were carefully evaluated: first, the question of any adverse effect was examined more closely with special regard to eventual oncogenity of growth factor application; second, the efficacy of intramyocardial FGF-1 injection was investigated during a three months follow up, with regard to changes in myocardial perfusion, cardiac function, and general clinical outcome of the patients.

20 patients with advanced coronary artery disease and no option for PTCA or CABG—verified by identical vote of cardiologist and cardiac surgeon—were included in this study (Table 1). All patients have had clinical evidence of inducible myocardial ischemia (angina), which was confirmed as well by ischemic ECG changes on stress testing as by proof of a reversible perfusion defect on single photon emission computed tomography (SPECT). Exclusion criteria included severe left ventricular dysfunction (ejection fraction (EF)<40%), recent myocardial ischemia, PTCA, or CABG within four months previously, any other concomitant heart disease like valve disease, renal insufficiency requiring dialysis, and a history of any kind of malignancy. Also, patients with proliferative retinopathy were excluded from the study. The study was performed at the Department of Thoracic & Cardiovascular Surgery, Fulda Medical Center, Germany. The protocol and patient consent form were approved by the responsible Ethical Commission & Human Investigation Committee of the University Marburg, Germany (Fd. St. 121/98). All patients provided written informed consent. Because of both, the severity of the underlying disease, and the necessity of a "control-thoracotomy" (without any treatment) in order to get a controlled study, we decided—in accordance with the responsible Ethical Commission & Human Investigation Committee—not to perform a controlled study, i.e., not to include a control group ("placebo-thoracotomy") in this clinical trial.

TABLE 1

Demographics, and preoperative and postoperative characteristics of the study population.

| Patients | Age (Years) | Previous Status (CCS) | Previous Procedures CABG | Previous Procedures PTCA | Region of Treatment | Clinical Outcome (CCS) |
|---|---|---|---|---|---|---|
| 1 | 69 | 3 | 1 | 0 | RCX | 1 |
| 2 | 66 | 3 | 2 | 0 | LAD | 2 |
| 3 | 65 | 3 | 0 | 0 | LAD | 2 |
| 4 | 60 | 4 | 1 | 1 | LAD | 3 |
| 5 | 61 | 4 | 1 | 1 | LAD | 2 |
| 6 | 52 | 3 | 1 | 0 | LAD/RCX | 2 |
| 7 | 69 | 3 | 1 | 1 | LAD | 1 |
| 8 | 50 | 3 | 0 | 0 | LAD/RCX | 1 |
| 9 | 70 | 3 | 1 | 0 | LAD | 2 |
| 10 | 73 | 3 | 0 | 1 | LAD | 2 |
| 11 | 62 | 3 | 1 | 0 | RCA | 2 |
| 12 | 77 | 3 | 1 | 0 | RCX | 2 |

TABLE 1-continued

Demographics, and preoperative and postoperative characteristics of the study population.

| Patients | Age (Years) | Previous Status (CCS) | Previous Procedures CABG | Previous Procedures PTCA | Region of Treatment | Clinical Outcome (CCS) |
|---|---|---|---|---|---|---|
| 13 | 72 | 3 | 0 | 0 | RCX | 2 |
| 14 | 65 | 3 | 2 | 0 | LAD | 2 |
| 15 | 62 | 3 | 1 | 1 | LAD | 2 |
| 16 | 50 | 4 | 1 | 0 | LAD | 4 |
| 17 | 60 | 3 | 0 | 1 | RCA | 2 |
| 18 | 66 | 2 | 0 | 0 | LAD/RCA | 2 |
| 19 | 62 | 3 | 1 | 0 | LAD/RCX | 2 |
| 20 | 58 | 3 | 0 | 0 | LAD/RCA | 2 |

CCS indicates Canadian Cardiovascular Society score;
CABG, coronary artery bypass grafting;
PTCA, coronary angioplasty;
LAD, left anterior descending coronary artery;
RCX, circumflex artery;
RCA, right coronary artery.

In this study, recombinant FGF-140 was used, that is, the 140 amino acid form of FGF-1 described above. Because it is known that FGF receptor activation requires heparin or heparan sulfate proteoglycans, 5,000 IE heparin per injection was added to the FGF-1(140) preparation Operative Procedure and FGF-1 Administration Following induction of general anesthesia, the left hemithorax was opened by a limited anterior thoracotomy in the $5^{th}$ intercostal space. After onset of single lung ventilation, the pericardium was incised in a longitudinal direction. With respect to the three main coronary arteries and their feeding territories (left anterior descending artery (LAD), circumflex artery (RCX), right coronary artery (RCA)), and according to the preoperative SPECT findings, the target regions (i.e. regions of reversible ischemia) of the myocardium were identified. FGF-1 (140) was injected (26 G syringe) into the myocardium with a dose per single injection of 0.01 mg/kg body weight combined with 5,000 units heparin (total volume of the injectate: 1.5 ml). 0.5 ml fibrin glue (Tissucol®) was then applied immediately to prevent FGF-1 leakage from the injection site. According to the study protocol, a maximum of three injections per patient was allowed. Following treatment, the pericardial incision was closed by three to four single absorbable sutures. After inserting a routine chest drain, the thoracotomy was closed in the usual manner. The patients were extubated in the operating room, and then transferred to the cardiac intermediate care unit for 24 hours routine monitoring. All patients were discharged from the hospital between days 3 to 5 postoperatively.

Follow Up

During the immediate postoperative course, the patients were submitted to routinely used hemodynamic monitoring including ECG, echocardiography, chest X-rays, and routine laboratory parameters. Cardiac isoenzymes and complete blood count were measured daily between day 1 and 5 postoperatively, and the chest tube was removed on the first postoperative day.

According to the study protocol, all patients underwent re-evaluation at day 45 (±3) and day 90 (±3) following FGF-1(140) treatment. As preoperatively, in all patients SPECT imaging at rest and stress, coronary angiography, echocardiography, ECG, chest X-ray, and exercise testing were performed. Also, serum chemistry, complete blood count, and coagulation parameters were evaluated. Additionally, the following tumor-markers were measured at days 45 and 90, and compared to the preoperative values: Carcinoembryogenic antigen (CEA) carbohydrate antigen (CA 19-9), Cytokeratin fragment (CYFRA 21-1), Alpha Fetoprotein (AFP), neuronal-specific enolase (NSE), Prostate-specific antigen (PSA). Eye examinations with special regard to alterations of the retina and corpus vitreum were performed by an experienced ophthalmologist.

SPECT Myocardial Perfusion Imaging

Standardized serial SPECT imaging using $^{99m}$Tc-sestamibi in all patients, were performed during rest and stress preoperatively and at follow up (days 45 and 90). 250 MBq $^{99m}$Tc-sestamibi were used for studying the patients at rest, 750 MBq for the stress examination (exercise stress test). All patient studies were acquired on a Siemans SPECT gamma camera, a conventional algorithm was applied for 3-D data reconstruction and display. Performance of myocardial perfusion at rest and stress was evaluated on short axis, vertical axis, and sagittal long axis slices, resulting in a set of 36 slices per investigation each. Regarding the region of interest, i.e. the myocardium having received the FGF-1(140) injection, a set of 4 short axis slices provided the basis for further evaluation by two blinded observers, using a visual semi-quantitative score, which ranged from 0 (=no perfusion) to 4 (=normal perfusion), modifying the technique according to Berman et al. (Berman, et al. (1993) *J. Am Coll Cardiol. vol.* 22:1455–1462). These scores were added to yield a summed rest score (SRS) and a summed stress score (SSS).

Exercise Protocol

Maximal working capacity of every individual patient was assessed by standardized bicycle exercise testing preoperatively (baseline), and at days 45 and 90. Strain was increased in 25 Watt intervals every two minutes. The maximum working capacity was determined as that level of work load that was obtained before either significant changes of ST-segments (>0.2 mV) or angina symptoms occurred.

Statistical Analysis

All data are expressed as mean ±SD. Continuous variables were compared using paired Student's t-test (baseline and follow up). A p value of <0.05 was considered statistically significant.

Patients 19 male patients aged between 50 and 77 years (mean: 63.4±7.17) and one 62 years old woman were included in the study (Table 1). All have had advanced and/or diffuse coronary artery disease not amenable for PTCA or CABG as voted independently by cardiologist and cardiac surgeon. Prior FGF-1 treatment, one patient was in class II according to Canadian Cardiovascular Society (CCS), 16 patients were in class III, and three patients in class IV. Previous CABG procedures were performed in 13 patients (twice in two of them), PTCA in 6 patients. There were 7 diabetic patients with three insulin-dependent, one patient received an AICD device two years previously due to recurrent ventricular fibrillation episodes.

Assessed by echocardiography and ventriculography, the left ventricular EF at baseline ranged from 40% to 85% (mean: 64.4±13.39). At baseline stress test, the maximal working capacity ranged from 50 watts to 150 watts (mean: 96.25±26.54). According to the baseline nuclear perfusion images prior to FGF-1(140) treatment, the areas of transient myocardial ischemia were identified as follows: LAD supplied area in 10 patients, RCX in three, and RCA in two, respectively. Three patients showed ischemia in both the LAD and RCX regions, two patients in both the LAD and RCA regions; thus, resulting in a total of 25 FGF-1$_{140}$ injections in 20 patients (Table 1).

There were no death or major complication throughout the total study course. The operation time lasted from 42 to 71 minutes (mean: 55.85±9.09). The heart rate and the mean arterial blood pressure remained basically unchanged during the operation and the postoperative period. Blood loss during operation was minimal, no patient required blood transfusion. In one patient atrial fibrillation occurred intra-operatively, with spontaneous recurrence of a regular sinus rhythm within 12 hours postoperatively. The postoperatively taken ECGs and the course of the values for the cardiac isoenzymes remained unchanged and showed no evidence for myocardial ischemia in any of the patients.

In all patients the chest drain could be removed within 24 hours postoperatively. In one patient a left pleural puncture was necessary on day 21 to remove 800 ml of sterile pleural effusion. One further patient suffered from a mild pericardial effusion on day 3 not requiring invasive treatment.

Serial echocardiography throughout the study course failed to show a statistically significant improvement of left ventricular function (EF): 64.4%±13.73 (baseline), 65.95±11.37 (day 45), 64.20±14.81 (day 90) (p=NS). Improvement in capillary density in the area of FGF-1$_{140}$ injection was noted by repeated standardized coronary angiography in all patients, but not evaluated quantitatively. However, there was not found any progress of coronary artery disease or plaque-progression in the native coronary vessels or bypass grafts.

Regarding the clinical status (CCS score) at day 90, 18 patients (90%) showed an improvement of at least one class; in four patients an improvement of even two classes could be demonstrated, in two patients the clinical status remained the same as preoperatively.

SPECT Myocardial Perfusion Imaging

Figure 16:
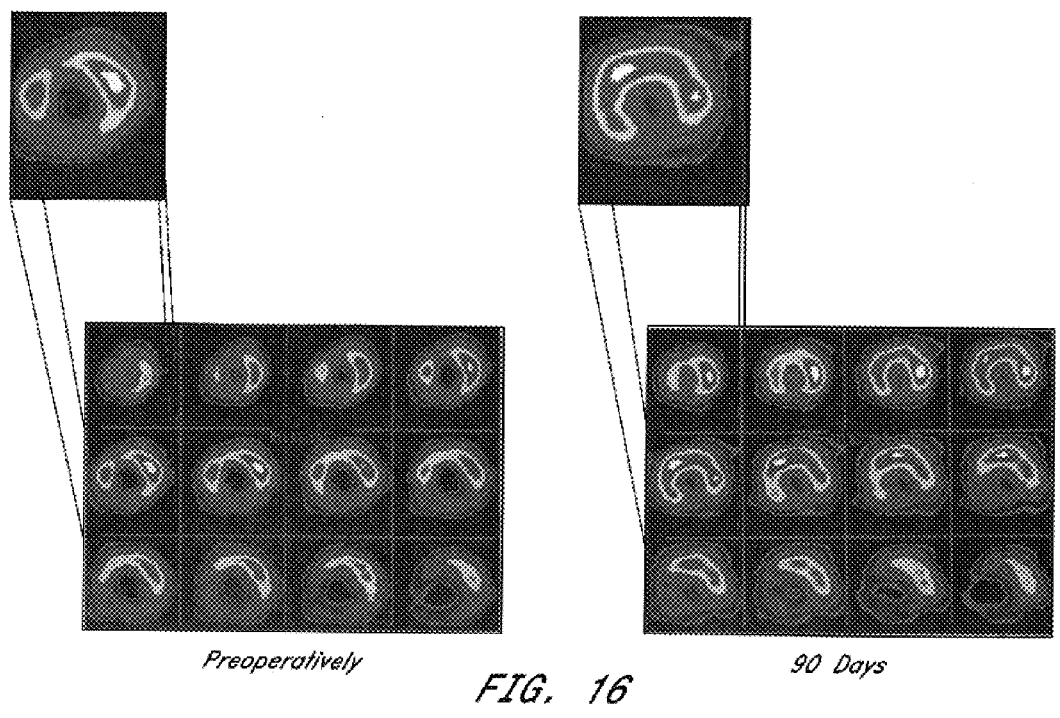
FIG. 16 shows stress SPECT $^{99m}$Tc-sestamibi scans in a study patient having received FGF-1 injection in the LAD area. Left, baseline (pre-treatment) scans; right, scans at day 90 (post-treatment). Improvement in primary stress perfusion defect.

A total of 120 sets of serial SPECT imaging slices, with 12 slices per investigation each, were evaluated (FIG. 16). In direct, blinded comparison particularly the treated myocardial areas (i.e. FGF-1$_{140}$ injection) were scored from 0 (=no perfusion) to 4 (=normal perfusion) comparing the baseline- and 45 days- and 90 days- images.

Regarding the SPECT images series taken at rest, in correspondence to the preoperative (baseline) images no significant changes could be detected during the whole study course (FIG. 17A): The summed rest score (SRS) for the areas of interest amounted from 14.70 (±1.34) at baseline to 14.90 (±1.21) at day 45, and to 15.25 (±0.91) at day 90 (p=NS). These findings excluded any adverse effect for the myocardial perfusion caused by the FGF-1$_{140}$ injection. In contrast to the SRS, the summed stress score (SSS) demonstrated a clear and significant improvement of myocardial perfusion within the treated area (FIG. 17B): 5.15±2.03 (baseline), 9.70±2.05 (day 45), 10.75±2.21 (day 90) (p<0.001). Following FGF-1$_{140}$ injection, 21 out of 25 treated areas (84%), or 16 out of the 20 patients (80%) showed that significant increase in tracer uptake during stress SPECT imaging throughout the study period—thus substantiating the increasing values of SSS in the study population (FIG. 16).

Working Capacity

An increase in maximal working capacity could be demonstrated in 16 out of the 20 patients (80%) following FGF-1$_{140}$ treatment. From the initial, preoperative mean working capacity of 96.25 (±26.54) Watts, the study group developed an increase of maximal working capacity up to 113.75 (±32.69) Watts at day 45 (p=NS), and further increasing up to 123.25 (±32.50) Watts at day 90 (p<0.001). 4 patients stayed on their pre-treatment level of maximal working capacity, however, a deterioration of working capacity did not occur in any of the patients.

Potential Adverse Effects of FGF-1$_{140}$ Delivery

As mentioned above, no death or major adverse effect could be ascertained during the whole study course. Focussing on the question of potential oncogenic effects following growth factor therapy, we carefully evaluated various tumor markers and their concentration in the serum throughout the study course (Table 2). Using 6 different, well established tumor markers, a wide spectrum of various malignancies was covered: CEA for gastro-intestinal tumors, CA 19-9 for pancreatic, gastric and colo-rectal cancer, CYFRA 21-1 for all types of lung cancer, particularly the squamous cell carcinoma, AFP for hepatocellular and non seminomal testicular carcinoma, NSE for all tumors of neuroectodermal and neuroendocrinal origin like insulinoma, carcinoid tumor, pheochromocytoma, neuroblastoma, and small cell lung carcinoma, and PSA for cancer of the prostate. With no exception, in all patients the levels of all tumor markers continued to stay in the normal range throughout the whole study course, not even a trend to elevation of every single tumor marker was detectable.

TABLE 2

Tumor markers. Serum values during study course.

| Tumormarker | Preoperatively | 6 Weeks | 12 Weeks | Normal Value |
|---|---|---|---|---|
| FP (µg/l) | 3.79 (±2.46) | 3.53 (±2.65) | 2.89 (±3.45) | <15 |
| SA (µg/l) | 1.69 (±2.04) | 1.68 (±2.40) | 1.27 (±2.27) | <4.0 |
| yfra (µg/l) | 0.68 (±0.39) | 0.67 (±0.37) | 0.64 (±0.54) | <3.3 |
| A19-9 (kU/l) | 7.46 (±7.15) | 7.65 (±7.72) | 4.57 (±5.71) | <37 |
| EA (pmol/l) | 10.21 (±4.77) | 9.67 (±4.54) | 6.77 (±6.06) | <25 |
| SE (µg/l) | 12.44 (±9.41) | 13.45 (±12.32) | 7.77 (±6.36) | <25 |

AFP indicates Alpha Fetoprotein;
PSA, Prostate-Specific Antigen;
CYFRA, Cytokeratin Fragment 21-1;
CA 19-9, Carbohydrat Antigen;
CEA, Carcinoembryogenic Antigen;
NSE, Neuronal-Specific Enolase.

Also, the serial ophtalmoscopic controls in all patients definitively could exclude any change of the status of the retina, the cornea, and the corpus vitreum, especially there was no indication of strengthened (neo-)vascularization in these tissues.

The data presented here, based on 20 patients treated by intramyocardial FGF-1 injection as sole therapy, demonstrate significant changes with regard to the post-treatment myocardial function: there was a significant improvement of myocardial perfusion in 80% of the patients (or in 84% of the treated myocardial areas), evaluated by serial stress SPECT—$^{99m}$Tc-sestamibi perfusion scans. In contrast, we saw no significant changes in the serial rest scans (SRS) during the study course; that is in close correspondence with the fact, that preferably those myocardial regions were effectively treated by FGF-1, which primarily have shown a perfusion defect at stress conditions. Also, this finding corresponds with the clinical symptomatology of most of our patients, i.e. angina at stress. Corresponding to the SPECT imaging data, also the maximal working capacity significantly increased in 80% of the patients during the follow up period of 90 days.

The present study demonstrates at first the safety and feasibility of intramyocardial FGF-1 protein delivery as sole therapy for patients not amenable to PTCA or CABG surgery—that concerning as well the surgical procedure as the theoretical risk of eventual oncogenity of FGF-1. Secondly, there is justified incentive from these phase I data, that intramyocardial FGF-1 application is able to improve myocardial perfusion and maximal working capacity of the treated patients. Looking forward, from our point of view intramyocardial application of angiogenic growth factors could emerge to a new treatment principle either as adjunct to bypass surgery or as sole therapy for patients with advanced coronary artery disease.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method for increasing cardiac efficiency of a heart having an ischemic myocardial region in a human subject, comprising the steps of:
   (a) preparing a pharmaceutical composition comprising a recombinant fibroblast growth factor-1 (FGF-1);
   (b) injecting an amount of said pharmaceutical composition into the ischemic region of the myocardium, said amount being sufficient to induce local neoangiogenesis; and
   (c) evaluating at least one clinical index of cardiac function to confirm that cardiac efficiency has increased.

2. The method of claim 1, wherein said FGF-1 is injected at a final concentration in a range of about 0.1 μg/kg body weight per site to about 10 μg/kg body weight per site.

3. The method of claim 1 wherein said FGF-1 is injected at a final concentration in a range of about 10 to 100 μg/kg body weight per site.

4. The method of claim 1, wherein the pharmaceutical composition further comprises a physiologic glue.

5. The method of claim 4, wherein said physiologic glue is fibrin glue.

6. The method of claim 1, wherein said FGF-1 and said physiologic glue are mixed immediately prior to application.

7. The method of claim 1, wherein said pharmaceutical composition further comprises an anticoagulant.

8. The method of claim 7, wherein said anticoagulant is heparin.

9. The method of claim 8, wherein the heparin is applied at a final concentration in a range of about 1 U per ml to about 1000 U per ml.

10. The method of claim 1, wherein said injecting step further comprises:
    making a thoracotomy incision;
    identifying at least one site of coronary artery stenosis;
    administering a β-blocker to reduce the heart rate to a range of about 20–60 beats per minute; and
    injecting the pharmaceutical composition intramyocardially at or near the at least one site of coronary artery stenosis.

11. The method of claim 10, wherein said thoracotomy incision further comprises an anterior left-sided incision; dissecting a region of costal cartilage over a 5$^{th}$ rib; and
    opening a left pleural space and a pericardium.

12. The method of claim 10, wherein the step of identifying the at least one site of coronary artery stenosis further comprises retracting the heart forward using traction sutures.

13. The method of claim 1, wherein the neoangiogenesis is long term and occurs in the ischemic region at 6 weeks after the injection.

14. The method of claim 1, wherein the neoangiogenesis is long term and occurs in the ischemic region at 3 months after the injection.

15. The method of claim 1, wherein the method further comprises performing a coronary artery bypass graft.

16. The method of claim 1, further comprising the step of injecting a composition comprising a physiologic glue subsequent to injection with the pharmaceutical composition.

17. The method of claim 1, wherein the ischemic region comprises at least one site in a heart wall.

* * * * *

UNITED STATES PATENT AND TRADEMARK OFFICE
CERTIFICATE OF CORRECTION

PATENT NO.       : 7,252,818 B2
APPLICATION NO.  : 10/649480
DATED            : August 7, 2007
INVENTOR(S)      : Thomas J. Stegmann It is certified that error appears in the above-identified patent and that said Letters Patent is hereby corrected as shown below:

On the Title Page Item (56), "Other Publications," add --Bauters, et al. Clinical Cardiology, 1997, vol. 20, pp II52-II57.--

On the Title Page Item (56), "Other Publications," Line 1, "Schumacher e tal." should be changed to --Schumacher et al.--

On the Title Page 2 Item (56), "Other Publications," Line 36, "Barrios, et al. "Angiogenesis in the rate heart" should be changed to --Barrios, et al. "Angiogenesis in the rat heart--

On the Title Page 2 Item (56), "Other Publications," Line 56, "and β form" should be changed to --and β forms--

On the Title Page 2 Item (56), "Other Publications," Line 57, "*Biochemica et*" should be changed to --*Biochimica et*--

On the Title Page 2 Item (56), "Other Publications," Line 65, "in an ishemic" should be changed to --in an ischemic--

On the Title Page 3 Item (56), "Other Publications," Line 7, "vol. 51, No. 1984," should be changed to --vol. 81, Nov. 1984,--

Column 5, Line 33, "embodiment, the the" should be changed to --embodiment, the--

Column 7, Line 4, "embodiment, the the" should be changed to --embodiment, the--

Column 8, Line 38, "interferon a2B;" should be changed to --interferon α2B;--

Column 11, Line 57, "obtain $Su^+$ derivatives" should be changed to --obtain $Su^°$ derivatives--

UNITED STATES PATENT AND TRADEMARK OFFICE
CERTIFICATE OF CORRECTION

PATENT NO.         : 7,252,818 B2
APPLICATION NO. : 10/649480
DATED                  : August 7, 2007
INVENTOR(S)       : Thomas J. Stegmann It is certified that error appears in the above-identified patent and that said Letters Patent is hereby corrected as shown below:

Column 12, Line 22, "*E. coli* Su+" should be changed to --*E. coli* Su$^+$--

Column 12, Line 28, "K 802 Su+." should be changed to --K 802 Su$^+$.--

Column 12, Line 57, "Then it infected" should be changed to --Then it is infected--

Column 18, Line 35, "Phage λ $cI_{857}$ $Qam_{117}$ $R_{am54}$" should be changed to --Phage λ $cI_{857}$ $Q_{am117}$ $R_{am54}$--

Column 19, Line 6, "phage λ $cI_{857}$ $Q_{am171}$" should be changed --phage λ $cI_{857}$ $Q_{am117}$--.

Column 20, Line 11, "Lanes I and 8" should be changed to --Lanes 1 and 8--

Column 20, Line 18, "in the Chicken Embrvo" should be changed to --in the Chicken Embryo--

Column 22, Line 59, "Exclusion of the Progenicity" should be changed to --Exclusion of the Pyrogenicity--

Column 23, Line 52, "HFGF-1 treatment" should be changed to --hFGF-1 treatment--

Column 23, Line 58, "Potency of HFGF-1" should be changed to --Potency of hFGF-l--

Column 25, Line 6, "recombinant HFGF-1" should be changed to --recombinant hFGF-1--

Column 25, Line 48, "improved vacularization" should be changed to --improved vascularization--

Column 25, Line 53, "whereas the the control" should be changed to --whereas the control--

UNITED STATES PATENT AND TRADEMARK OFFICE
CERTIFICATE OF CORRECTION

PATENT NO. : 7,252,818 B2
APPLICATION NO. : 10/649480
DATED : August 7, 2007
INVENTOR(S) : Thomas J. Stegmann It is certified that error appears in the above-identified patent and that said Letters Patent is hereby corrected as shown below:

Column 25, Line 61, "was suprising in view" should be changed to --was surprising in view--

Column 26, Line 3, "Use of Recombinant HFGF-1" should be changed to --Use of recombinant hFGF-1--

Column 27, Line 41, "glue (Tissucol®" should be changed to --glue (Tissucol®)--

Column 30, Line 43, "CA 19-9, Carbohydrat Antigen;" should be changed to --CA 19-9, Carbohydrate Antigen,--

Column 30, Line 45, "the serial ophtalmoscopic" should be changed to --the serial ophthalmoscopic--

Signed and Sealed this

Eleventh Day of December, 2007

JON W. DUDAS
*Director of the United States Patent and Trademark Office*